(12) United States Patent
Yun et al.

(10) Patent No.: US 7,738,952 B2
(45) Date of Patent: *Jun. 15, 2010

(54) TREATMENT OF CONDITIONS THROUGH MODULATION OF THE AUTONOMIC NERVOUS SYSTEM

(75) Inventors: Anthony Joonkyoo Yun, Palo Alto, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 1379 days.

This patent is subject to a terminal disclaimer.

(21) Appl. No.: 11/060,643

(22) Filed: Feb. 16, 2005

(65) Prior Publication Data

US 2005/0240241 A1    Oct. 27, 2005

Related U.S. Application Data

(63) Continuation-in-part of application No. 10/871,366, filed on Jun. 18, 2004, now Pat. No. 7,363,076, which is a continuation-in-part of application No. 10/661,368, filed on Sep. 12, 2003, now Pat. No. 7,149,574.

(60) Provisional application No. 60/547,955, filed on Feb. 25, 2004, provisional application No. 60/477,070, filed on Jun. 9, 2003, provisional application No. 60/482,593, filed on Jun. 24, 2003, provisional application No. 60/494,260, filed on Aug. 11, 2003.

(51) Int. Cl.
*A61N 1/00* (2006.01)
(52) U.S. Cl. .......................................... 607/2
(58) Field of Classification Search ................ 607/1, 607/2, 45, 40
See application file for complete search history.

(56) References Cited

U.S. PATENT DOCUMENTS

| | | |
|---|---|---|
| 5,188,104 A | 2/1993 | Wernicke et al. |
| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,330,515 A | 7/1994 | Rutecki et al. |
| 5,335,657 A | 8/1994 | Terry, Jr. et al. |
| 5,540,730 A | 7/1996 | Terry, Jr. et al. |
| 5,571,150 A | 11/1996 | Wernicke et al. |
| 5,707,400 A | 1/1998 | Terry, Jr. et al. |
| 5,978,702 A | 11/1999 | Ward et al. |
| 6,253,109 B1 | 6/2001 | Gielen |
| 6,319,241 B1 | 11/2001 | King et al. |
| 6,337,997 B1 | 1/2002 | Rise |
| 6,356,784 B1 | 3/2002 | Lozano et al. |
| 6,366,813 B1 | 4/2002 | DiLorenzo |
| 6,459,936 B2 | 10/2002 | Fischell et al. |
| 6,480,743 B1 | 11/2002 | Kirkpatrick et al. |
| 6,484,059 B2 | 11/2002 | Gielen |
| 6,526,318 B1 | 2/2003 | Ansarinia |
| 6,609,025 B2 | 8/2003 | Barrett et al. |
| 7,162,303 B2 * | 1/2007 | Levin et al. .................. 607/44 |
| 2002/0177882 A1 | 11/2002 | DiLorenzo |
| 2003/0018367 A1 | 1/2003 | DiLorenzo |
| 2003/0144709 A1 | 7/2003 | Zabara et al. |
| 2004/0210261 A1 * | 10/2004 | King et al. .................... 607/9 |

* cited by examiner

*Primary Examiner*—Scott M Getzow
(74) *Attorney, Agent, or Firm*—Bret E. Field; Bozicevic, Field & Francis LLP

(57) ABSTRACT

Methods are provided for treating a subject for a condition by modulating at least a portion of the subject's autonomic nervous system. In accordance with certain embodiments of the subject methods, at least a portion of a subject's autonomic nervous system is electrically or pharmacologically modulated in a manner that is effective to treat the subject for the condition. The subject methods find use in the treatment of a variety of different conditions, where such conditions include various disease conditions. Also provided are systems and kits for use in practicing the subject methods.

5 Claims, No Drawings

TREATMENT OF CONDITIONS THROUGH MODULATION OF THE AUTONOMIC NERVOUS SYSTEM

CROSS REFERENCE TO RELATED APPLICATIONS

The present application claims priority under 35 U.S.C. §119(e) to U.S. provisional application No. 60/547,955 filed Feb. 25, 2004 and is a continuation-in-part application of application Ser. No. 10/871,366 filed Jun. 18, 2004, which application is a continuation-in-part application of application Ser. No. 10/661,368 filed Sep. 12, 2003, which application claims priority under 35 U.S.C. §119(e) to U.S. provisional application No. 60/477,070 filed Jun. 9, 2003, to U.S. provisional application No. 60/482,593 filed Jun. 24, 2003 and to U.S. provisional application No. 60/494,260 filed Aug. 11, 2003, the disclosures of which are incorporated herein by reference in their entirety.

INTRODUCTION

1. Field of the Invention

The field of this invention is the treatment of conditions associated with the autonomic nervous system and more specifically the treatment of conditions through modulation of the autonomic nervous system.

2. Background of the Invention

There are a variety of conditions that can affect an individual's health and well-being. The treatment of such various conditions has been around for centuries. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative. In fact, treatment protocols effectively directed at the underlying cause of a condition are quite rare.

As such, there continues to be an interest in the development of new protocol options for treating conditions. Of particular interest are protocols for treating conditions that are directed at the cause of the condition rather than the symptoms thereof.

3. References of Interest

References of interest include U.S. Pat. No. 6,526,318.

SUMMARY OF THE INVENTION

Methods are provided for treating a subject for a condition by modulating at least a portion of the subject's autonomic nervous system. In accordance with certain embodiments of the subject methods, at least a portion of a subject's autonomic nervous system is electrically or pharmacologically modulated in a manner that is effective to treat the subject for the condition. Certain embodiments include electrically or pharmacologically modulating at least a portion of a subject's autonomic nervous system by decreasing and/or increasing parasympathetic and/or sympathetic activity in at least a portion of the subject's autonomic nervous system. In certain embodiments, modulation may include increasing the parasympathetic activity/sympathetic activity ratio in at least a portion of the subject's autonomic nervous system. In certain embodiments, modulation may include increasing the sympathetic activity/parasympathetic activity ratio in at least a portion of the subject's autonomic nervous system. In certain embodiments, both electrical and pharmacological modulation are employed. The subject methods find use in the treatment of a variety of different conditions, where such conditions include various disease conditions. Also provided are systems and kits for use in practicing the subject methods.

DETAILED DESCRIPTION OF THE INVENTION

Methods are provided for treating a subject for a condition by modulating at least a portion of the subject's autonomic nervous system. In accordance with certain embodiments of the subject methods, at least a portion of a subject's autonomic nervous system is electrically or pharmacologically modulated in a manner that is effective to treat the subject for the condition. Certain embodiments include electrically or pharmacologically modulating at least a portion of a subject's autonomic nervous system by decreasing and/or increasing parasympathetic and/or sympathetic activity in at least a portion of the subject's autonomic nervous system. In certain embodiments, modulation may include increasing the parasympathetic activity/sympathetic activity ratio in at least a portion of the subject's autonomic nervous system. In certain embodiments, modulation may include increasing the sympathetic activity/parasympathetic activity ratio in at least a portion of the subject's autonomic nervous system. In certain embodiments, both electrical and pharmacological modulation are employed. The subject methods find use in the treatment of a variety of different conditions, where such conditions include various disease conditions. Also provided are systems and kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Methods

As noted above, the subject methods are methods for treating a subject for a condition by modulating at least a portion of the subject's autonomic nervous system in a manner sufficient to treat the condition. In many embodiments, the subject methods are employed to treat a condition that is caused by an abnormality in the subject's autonomic nervous system. Embodiments of the subject methods are methods for treating a subject for a condition caused by an abnormality in a subject's autonomic nervous system by modulating at least a portion of the subject's autonomic nervous system by any suitable method, e.g., by electrically modulating and/or pharmacologically modulating, at least a portion of the autonomic nervous system, in a manner effective to treat the subject for the condition. In certain embodiments, modulation of at least a portion of a subject's autonomic nervous system includes increasing the parasympathetic activity/sympathetic activity ratio.

The autonomic nervous system may be modulated using any suitable technique, including, but not limited to, surgical methods (e.g., surgical isolation of an effector structure from sympathetic and/or parasympathetic innervation, i.e., surgically isolating an effector structure from one or more sympathetic and/or parasympathetic nerve fibers associated with it); ablation (permanently or reversibly ablating a nerve by employing energy delivery devices or cryotherapy); cryoablation; thermoablation; microwave energy; focus ultrasound; magnetic fields including internal and external magnetic fields; laser energy; optical energy; radiofrequency energy; pacing mechanisms (e.g., implantable electrode-based pacing systems, external magnetic-based pacing system, and the like); transcutaneous electrical nerve stimulation ("TENS") or transmagentic stimulation ("TMS") (see for example George, M. Stimulating the Brain. Sci Amer September 2003); pharmacological modulation and electrical modulation.

Embodiments of the subject invention includes modulating at least a portion of a subject's autonomic nervous system to increase the parasympathetic activity/sympathetic activity ratio, i.e., increase parasympathetic activity relative to sympathetic activity. In accordance with the subject invention, increasing the parasympathetic activity/sympathetic activity ratio may be achieved by stimulating the parasympathetic system to increase activity in at least a portion of the parasympathetic system, e.g., stimulating at least one parasympathetic nerve fiber. Alternatively or in addition to stimulating at least one parasympathetic nerve fiber to increase activity, increasing the parasympathetic activity/sympathetic activity ratio may be achieved by inhibiting activity in the sympathetic system, e.g., inhibiting activity in at least one sympathetic nerve fiber. While the subject methods are described primarily with respect to embodiments that result in increasing the parasympathetic activity/sympathetic activity ratio, it is to be understood that the subject invention is not limited to embodiments wherein the parasympathetic activity/sympathetic activity ratio is increased and as such include embodiments for modulating at least a portion of a subject's autonomic nervous system to decrease the parasympathetic activity/sympathetic activity ratio, i.e., decrease parasympathetic activity relative to sympathetic activity, and the like.

Embodiments of the subject methods may include providing electrical energy (electrical modulation) to at least a portion of a subject's autonomic nervous system, where such electrical energy may be excitatory or inhibitory and in certain embodiments may include both excitatory and inhibitory stimulation. Embodiments of the subject methods may include administering at least one pharmacological agent (pharmacological modulation) to said subject to modulate at least a portion of a subject's autonomic nervous system, where the pharmacological agent may be employed to increase activity in at least a portion of the autonomic nervous system and/or decrease activity in at least a portion of the autonomic nervous system Embodiments of the subject invention may include electrically modulating (i.e., applying electrical energy to) at least a portion of a subject's autonomic nervous system and/or pharmacologically modulate at least a portion of the autonomic nervous system to achieve a desired parasympathetic activity/sympathetic activity ratio, i.e., a desired balance between parasympathetic activity and sympathetic activity. In certain embodiments the desired ratio is analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods may be analogous to the parasympathetic activity/sympathetic activity ratio observed in a healthy human ranging in age from about 20 years old to about 25 years old.

As indicated above, embodiments of the subject invention may include treating a subject for a condition caused by an abnormality in the subject's autonomic nervous system by electrically modulating at least a portion of the subject's autonomic nervous system, e.g., to increase the parasympathetic activity/sympathetic activity ratio or increase parasympathetic activity relative to sympathetic activity. By "electrically modulating at least a portion of a subject's autonomic nervous system" is meant altering or changing at least a portion of an autonomic nervous system by electrical means to provide a change, alteration or shift in at least one component or aspect of the autonomic nervous system, as will be described in greater detail below. The modulation of the autonomic nervous system may affect central motor output and/or nerve conduction and/or transmitter release and/or synaptic transmission and/or receptor activation, and in many embodiments is a change that provides an increase in the parasympathetic activity/sympathetic activity ratio (as used herein, "activity" and "function" are used interchangeably). For example, at least a portion of the autonomic nervous system may be electrically modulated to alter, shift or change parasympathetic activity and/or sympathetic activity from a first state to a second state, where the second state is characterized by an increase in the parasympathetic activity/sympathetic activity ratio relative to the first state. In certain embodiments, the subject invention provides methods of increasing activity in at least one parasympathetic nerve fiber to achieve an increase in the parasympathetic activity/sympathetic activity ratio. In certain embodiments the subject invention provides methods of inhibiting activity in at least one sympathetic nerve fiber to achieve an increased parasympathetic activity relative to sympathetic activity. Still further, in certain embodiments the subject invention provides methods of both increasing activity in at least one parasympathetic nerve fiber and inhibiting activity in at least one sympathetic nerve fiber to achieve the desired result. Certain embodiments include electrically stimulating, e.g., with long-term low frequency stimulation, to inhibit or depress activity in the sympathetic nervous system.

Embodiments of the subject invention may include treating a subject for a condition caused by an abnormality in the subject's autonomic nervous system by pharmacologically modulating at least a portion of the subject's autonomic nervous system, e.g., to increase the parasympathetic activity/sympathetic activity ratio or increase parasympathetic activity relative to sympathetic activity. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system, as will be described in greater detail below. The modulation of the autonomic nervous system may affect central motor output and/or nerve conduction and/or transmitter release and/or synaptic transmission and/or receptor activation, and in many embodiments is a change that provides an increase in the parasympathetic activity/sympathetic activity ratio (as used herein, "activity" and "function" are used interchangeably). For example, at least a portion of the autonomic nervous system may be pharmacologically modulated to alter, shift or change parasympathetic activity and/or sympathetic activity from a first state to a second state, where the second state is characterized by an increase in the parasympathetic activity/sympathetic activity ratio relative to the first state. In certain embodiments, the subject invention provides methods of increasing activity in at least one parasympathetic nerve fiber to achieve an increase in the parasympathetic activity/sympathetic activity ratio. In certain embodiments the subject invention provides methods of inhibiting activity in at least one sympathetic nerve fiber to achieve an increased parasympathetic activity relative to sympathetic activity. Still further, in certain embodiments the subject invention provides methods of both increasing activity in at least one parasympathetic nerve fiber and inhibiting activity in at least one sympathetic nerve fiber to achieve the desired result.

Accordingly, in certain embodiments of the subject methods the parasympathetic activity/sympathetic activity ratio is increased. By "increased ratio of parasympathetic activity to sympathetic activity" and analogous terms is meant that this ratio is increased in at least a portion of the autonomic nervous system, where the increase is at least great enough to treat a given condition.

While the ratio of sympathetic function/parasympathetic function may be increased according to embodiments of the subject invention, the net result may be a sympathetic bias (i.e., sympathetic dominance), parasympathetic bias (i.e., parasympathetic dominance) or the activities of the sympathetic system and parasympathetic system may be substantially equal (i.e., neither is dominant). By "bias" is meant that the particular "biased" component of the autonomic nervous system has a higher activity level than the other component. For example, a sympathetic bias refers to a higher level of sympathetic activity than parasympathetic activity, and vice versa, where such bias may be systemic or localized. The net result of the subject methods to treat a condition may be higher or greater sympathetic activity relative to parasympathetic activity in at least the area of the autonomic system targeted or rather in need of modulation, higher or greater parasympathetic activity relative to sympathetic activity in at least the area of the autonomic system targeted or rather in need of modulation, or substantially equal activity levels of sympathetic activity and parasympathetic activity.

In practicing the subject methods, at least a portion of a subject's autonomic nervous system is modulated, e.g., electrically and/or pharmacologically. Modulation according to the embodiments of the subject methods may result in an increase in parasympathetic activity relative to sympathetic activity (i.e., increase parasympathetic activity/sympathetic activity ratio). As noted above, the electrical and/or pharmacological modulation may provide an increase in function of at least a portion of the autonomic system, e.g., increase function in at least one parasympathetic nerve fiber, and/or provide a decrease in function or dampening of a portion of the autonomic system, e.g., may inhibit activity in at least one sympathetic nerve fiber or inhibit nerve pulse transmission.

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ or even to a particular nerve fiber. For example, localization may be with respect to innervations of one or more organs. Area(s) of the autonomic nervous system that may be include, but are not limited to, pre- and post ganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber.

Embodiments of the subject methods may include determining and/or monitoring one or more indicators, effects or results of the autonomic nervous system. For example, the level of T helper cells (Th1 and/or Th2), and the like, may be monitored, e.g., as an indicator of the parasympathetic activity/sympathetic activity ratio. Such may be monitored at any suitable time including before, during and after modulating the autonomic nervous system in accordance with the subject invention.

As will be described in greater detail below, any part of the subject methods may be performed manually or automatically.

Increasing Activity in at Least a Portion of the Autonomic Nervous System

As noted above, in certain embodiments activity in at least a portion of the autonomic nervous system is increased. For example, any portion of the parasympathetic system, e.g., one or more nerve fibers, may be electrically and/or pharmacologically stimulated to increase parasympathetic activity to provide the desired ratio of parasympathetic/sympathetic activity. In other words, activity in at least a portion of the parasympathetic nervous system may be increased electrically and/or pharmacologically such that at least a portion of the parasympathetic nervous system may be "up-regulated". Likewise, any portion of the sympathetic system, e.g., one or more nerve fibers, may be electrically and/or pharmacologically stimulated to provide the desired ratio of parasympathetic/sympathetic activity. In other words, activity in at least a portion of the sympathetic nervous system may be increased electrically and/or pharmacologically such that at least a portion of the sympathetic nervous system may be "up-regulated".

In certain embodiments, increasing activity in, or up-regulating, at least a part of the parasympathetic system may be desired in instances where, prior to the application of autonomic nervous system-modulating electrical energy and/or the administration of an effective amount of at least one pharmacological agent, sympathetic activity is higher than desired, e.g., higher than parasympathetic activity (e.g., there exists a relative sympathetic bias) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a sympathetic bias, parasympathetic bias or may be an equalization of the two systems (i.e., the activities of the two systems are approximately equal-including equal), but the difference between the parasympathetic-sympathetic systems may be modulated, e.g., reduced or minimized or increased in certain embodiments. Accordingly, the subject methods may be employed to increase parasympathetic activity above that of sympathetic activity and/or may be employed to modulate (increase or decrease) the differential between the two systems, but in certain embodiments may be employed to increase the parasympathetic activity/sympathetic activity ratio.

In those instances where there exists a sympathetic bias prior to increasing parasympathetic activity, the cause of the sympathetic bias may be manifold, e.g., hyperthermia, infection, inflammation and fever, and the like may be causes of sympathetic bias.

In certain embodiments, a sympathetic bias may be the normal state, but the ratio of the two systems may be abnormal or otherwise contributing to a condition. Increasing parasympathetic bias may also be desired in instances where, prior to the application of autonomic nervous system-modulating electrical energy and/or the administration of an effective amount of at least one pharmacological agent, parasympathetic activity is higher than the sympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low). For example, such instances may occur where a subject has normal or above normal parasympathetic function, but also has elevated sympathetic function. Other instances may include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing parasympathetic activity may be desired will be apparent to those of skill in the art.

While the subject methods are described primarily with respect to increasing activity in the parasympathetic system, it is to be understood that this is for exemplary purposes only and is in no way intended to limit the scope of the invention as activity may also, or in addition, be increased in at least a portion of the sympathetic nervous system.

Inhibiting Activity in at Least a Portion of the Autonomic Nervous System

As noted above, in certain embodiments activity in at least a portion of the sympathetic system may be inhibited to modulate at least a portion of the autonomic nervous system. For example, activity in any portion of the sympathetic nervous system may be inhibited, e.g., to provide the desired ratio of parasympathetic/sympathetic activity, e.g., activity in one or more sympathetic nerve fibers may be inhibited. Likewise, activity in at least a portion of the parasympathetic system may be inhibited to modulate at least a portion of the autonomic nervous system. For example, activity in any portion of the parasympathetic nervous system may be inhibited, e.g., to provide the desired ratio of parasympathetic/sympathetic activity, e.g., activity in one or more parasympathetic nerve fibers may be inhibited. By "inhibited" is meant to include disruption, down-regulating, dampening and partial and complete blockage of nerve impulses in a particular area of the autonomic nervous system.

Inhibiting or "down-regulating" activity in at least a part of the autonomic nervous system, e.g., in at least a portion of the sympathetic system, may be desired in instances where, prior to the inhibition of activity in, e.g., at least one sympathetic nerve fiber, the sympathetic activity is higher than desired. For example, sympathetic activity may be higher than the parasympathetic activity (i.e., there exists a sympathetic bias) or sympathetic activity may be less than or approximately equal to, including equal, to parasympathetic activity, and the subject methods may be employed to modulate the differential between the parasympathetic-sympathetic systems such that the result of decreasing,sympathetic activity may be a sympathetic bias, parasympathetic bias or may be an equalization of the two systems (i.e., the activities of the two systems are approximately equal-including equal), but the difference between the parasympathetic-sympathetic systems may be modulated, e.g., increased or reduced in certain embodiments. Accordingly, the subject methods may be employed to decrease sympathetic activity below that of sympathetic activity and/or may be employed to modulate (decrease or increase) the differential between the two systems, where in certain embodiments may be employed to increase the ratio of parasympathetic activity to sympathetic activity.

For example, decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one sympathetic nerve fiber, parasympathetic activity is higher than the sympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing sympathetic activity may be desired is exemplary only and is in no way intended to limit the scope of the invention and other instances where decreasing sympathetic activity to provide an increase in the parasympathetic activity/sympathetic activity ratio may be desired will be apparent to those of skill in the art.

Inhibiting or down-regulating at least a portion of the autonomic nervous system may be accomplished in a number of ways. For example, inhibition or down-regulation of activity may be achieved by surgically isolating an effector structure (i.e., the target of the sympathetic activity) from sympathetic innervation, i.e., surgically isolating an effector structure from one or more sympathetic nerve fibers associated with it. Furthermore, sympathetic nerves may be ablated, permanently or reversibly, by employing energy delivery devices or cryotherapy. Certain embodiments may employ cryoablation, thermoablation, microwave energy, focus ultrasound, magnetic fields including internal and external magnetic fields, laser energy, optical energy, radiofrequency energy, and the like. The sympathetic system may also be inhibited or down-regulated or depressed by employing pacing mechanisms such as implantable electrode-based pacing systems, external magnetic-based pacing system, and the like. Certain embodiments may include inhibiting activity in at least a portion of the sympathetic nervous system using transcutaneous electrical nerve stimulation ("TENS") or transmagentic stimulation ("TMS") (see for example George, M. Stimulating the Brain. Sci Amer September 2003). Still further, one or more pharmacological agents may be employed to disable sympathetic and/or paraympathetic function, e.g., such that the parasympathetic to sympathetic ratio is increased temporarily or permanently.

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ or even to a particular nerve fiber. For example, localization may be with respect to innervations of one or more organs.

Embodiments of the subject methods may include determining and/or monitoring one or more indicators, effects or results of the autonomic nervous system. For example, the level of T helper cells (Th1 and/or Th2), and the like, may be monitored, e.g., as an indicator of the parasympathetic activity/sympathetic activity ratio. Such may be monitored at any suitable time including before, during and after modulating the autonomic nervous system in accordance with the subject invention.

While the subject methods are described primarily with respect to decreasing activity in the sympathetic system, it is to be understood that this is for exemplary purposes only and is in no way intended to limit the scope of the invention as activity may also, or in addition, be decreased in at least a portion of the parasympathetic nervous system.

Increasing Activity in at Least a Portion of the Autonomic Nervous System and Inhibiting Activity in at Least a Portion of the Autonomic Nervous System As noted above, in certain embodiments activity in at least a portion of the autonomic nervous system may be increased and activity in at least a portion of the autonomic nervous system may be decreased. For example, in certain embodiments activity in at least a portion of the parasympathetic system may be increased and activity in at least a portion of the sympathetic system may be inhibited, e.g., to increase the parasympathetic activity/sympathetic activity ratio. As described above, any portion of the parasympathetic and/or sympathetic nervous systems may be electrically and/or pharmacologically modulated to increase activity and activity in any portion of the sympathetic and/or parasympathetic nervous system may be inhibited to provide the desired ratio of parasympathetic activity to sympathetic activity. Such a protocol may be employed, e.g., in instances where parasympathetic function is normal or abnormally low and/or sympathetic function is normal or abnormally high where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the sympathetic system may be higher than activity in the parasympathetic system and the subject methods may be employed to increase the parasympathetic activity to a level that is greater than the sympathetic activity and/or may be employed to alter the differential or difference in activity levels of the two systems such as decreasing the difference in activity levels or increasing the difference in activity levels. In other embodiments, prior to modulating the autonomic system according to the subject invention, the activity in the parasympathetic system may be higher than activity in the sympathetic system and the subject methods may be employed to alter the differential or difference in activity levels of the two systems such as increasing the difference in activity levels. The above-described examples of instances where increasing activity in at least a portion of the parasympathetic system and decreasing activity in at least a portion of the sympathetic activity may be desired is exemplary only and is in no way intended to limit the scope of the invention and other instances where increasing activity in at least a portion of the parasympathetic system and decreasing activity in at least a portion of the sympathetic activity may be desired will be apparent to those of skill in the art.

Increasing activity in at least a portion of the autonomic nervous system, e.g., increasing activity in at least a portion of the parasympathetic system, and decreasing activity in at least a portion of the autonomic nervous system, e.g., decreasing activity in at least a portion of the sympathetic system, may be performed simultaneously or sequentially such that at least a portion of the autonomic nervous system, e.g., at least a portion of the parasympathetic nervous system, may be electrically and/or pharmacologically modulated to increase activity therein prior or subsequent to inhibiting activity in at least a portion of the autonomic nervous system e.g., at least a portion of the sympathetic nervous system, such as by electrical and/or pharmacological means.

Regardless of whether increasing activity in at least a portion of the autonomic nervous system, e.g., in at least a portion of the parasympathetic system, and decreasing activity in at least a portion of the autonomic nervous system, e.g., in at least a portion of the sympathetic system, is performed simultaneously or sequentially, the parameters for increasing activity in at least a portion of autonomic nervous system and decreasing activity in at least a portion of the autonomic nervous system may be analogous to that described above.

As noted above, modulation of at least a portion of the autonomic nervous system to treat a condition may be accomplished in any suitable manner, where electrical and pharmacological modulation are two exemplary methods that may be employed in the practice of the subject methods. Each of these are now described in greater detail.

Pharmacological Modulation of at Least a Portion of the Autonomic Nervous System As described above, embodiments include treating a subject for a condition by pharmacologically modulating at least a portion of the subject's autonomic nervous system, e.g., to increase the parasympathetic activity/sympathetic activity ratio. Accordingly, one or more pharmacological agents may be employed to increase and/or decrease activity in at least a portion of the autonomic nervous system. For example, embodiments may include administering one or more pharmacological agents to achieve one or more of the: (1) increasing activity in at least one sympathetic nerve fiber to achieve an increase in activity at least a portion of the sympathetic system, (2) increasing activity in at least one parasympathetic nerve fiber to achieve an increase in activity in at least a portion of the parasympathetic system, (3) inhibiting activity in at least one sympathetic nerve fiber to achieve a decease in activity at least a portion of the sympathetic system, and (4) inhibiting activity in at least one parasympathetic nerve fiber to achieve a decease in activity in at least a portion of the parasympathetic system.

Certain embodiments of the subject invention may include administering an effective amount of one or more pharmacological agents to both increase activity in at least a portion of the autonomic nervous system, e.g., increase activity in at least one parasympathetic nerve fiber, and inhibit activity in at least a portion of the autonomic nervous system, e.g., inhibit activity in at least one sympathetic nerve fiber, or vice versa, to treat a condition.

Pharmacological modulation in accordance with the subject invention may be performed prior to and/or at the same time and/or subsequent to any other medical or clinical treatment regime such as any one or more of those described above, for example, electrical modulation of at least a portion of the subject's autonomic nervous system, e.g., as described in copending U.S. patent application Ser. No. 10/661,368, entitled "Treatment of Conditions Through Electrical Modulation of the Autonomic Nervous System", the disclosure of which is herein incorporated by reference, and the like. In other words, the subject methods may include other concomitant therapies or treatments to treat the same condition or a different condition.

According to embodiments of the subject invention, pharmacological modulation may be accomplished by at least administering an effective amount of at least one pharmacological agent to a subject to modulate at least a portion of the autonomic nervous system in a manner sufficient to treat the subject for a condition, where the condition being treated may be one that is caused, precipitated or otherwise exacerbated, influenced or affected by the ratio of parasympathetic activity/sympathetic activity ratio. In other words, activity in at least a portion of the autonomic nervous system may be at a level that is at least contributing to or otherwise affecting or exacerbating a condition such a disease condition in need of treatment, and as such modulation of the autonomic nervous system may be employed to treat the condition.

That is, embodiments of the subject methods include administering an effective amount, i.e., a therapeutically effective amount, of one or more pharmacological agents to a subject to modulate at least a portion of the subject's autonomic nervous system. By "effective amount" and analogous terms is meant a dosage sufficient to modulate at least a portion of a subject's autonomic nervous system for a given period of time. The effective amount will vary with the age and physical condition of the subject, type and severity of the condition being treated, the duration of the treatment, the nature of any concurrent treatment, the pharmaceutically acceptable carrier used if any, and analogous factors within the knowledge and expertise of those skilled in the art. Introduction of an effective amount of a pharmacological agent to a subject resulting in a modulation of at least a portion of the autonomic nervous system may be a temporary or permanent change in the autonomic nervous system. In certain embodiments, more than one type of pharmacological agent may be administered at the same or different time as another pharmacological agent to treat a female for the same or different condition.

The effective amount of a given pharmacological agent may vary somewhat from subject to subject, and may depend upon factors such as, but not limited to, the age and condition of the subject, the form of the pharmacological agent, the route and method of delivery, etc., as noted above. Such dosages may be determined in accordance with routine pharmacological procedures known to those skilled in the art. Pharmacological agent and/or adjuvants may be administered to a subject in a single oral dose, one time a day or more for days, weeks, months, years, even as long as a subject's lifetime. For example, embodiment may include administering a given pharmacological agent one time a day over a prolonged period of time, e.g., over about 1 week, e.g., over about 1-3 months, e.g., about 3 months to about 3 years or more, e.g., orally or with a medical infusion pump or similar device designed for delivery of a substance over a prolonged period. The frequency of administration of a pharmacological agent may vary depending, e.g., on one or more of the factors described above. For example, the frequency of administration may range from about 1 time per day to multiple times per day, e.g., about 2 times or more per day or as necessary to treat or otherwise control or manage a condition. The duration of therapy depends on the type of condition being treated and may range from as short as about 24 hours to as long as the life of the subject. By "adjuvants" is meant a compound that, when used in combination with the one or more pharmacological agent compounds and/or compositions, augments or otherwise alters or modifies the resultant pharmacological and/or physiological responses.

Embodiments may include daily discrete or continuous unit doses wherein the total number of daily units may be equal to the total number of days of a given week, month, or the like, e.g., in the form of a pack. For example, embodiments may include daily discrete or continuous unit doses wherein the total number of daily units may be equal to the total number of days of a week or month, e.g., in the form of a monthly pack.

Depending on the particular pharmacological agent administered to a subject, the pharmacological agent may be administered to a subject using any convenient means capable of resulting in the desired modulation of the autonomic nervous system. Thus, the at least one pharmacological agent may be incorporated into a variety of formulations for therapeutic administration. More particularly, the pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the particular pharmacological agent and other optional ingredients of the subject pharmacological agent compositions in that a pharmaceutically acceptable carrier may be combined with the pharmacological agent without eliminating the biological or therapeutically effective activity of the pharmacological agent, and is suitable for use in subjects as provided herein without undue adverse side effects (such as toxicity, irritation, allergic response, and death). Side effects are "undue" when their risk outweighs the benefit provided by the pharmacological agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agent employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, a given pharmacological agent may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an pharmacological formulations may be prepared by any suitable method of pharmacy which includes, but is not limited to, bringing into association the active pharmacological agent and a suitable carrier (which may contain one or more optional ingredients as noted above). For example, pharmacological formulations for use with the subject invention may be prepared by uniformly and intimately admixing the active pharmacological agent with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

A pharmacological agent of this invention may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include a pharmacological agent made into suppositories by mixing with a variety of bases such as emulsifying bases or water-soluble bases.

A pharmacological agent of used in the practice of the subject methods may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include a pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, a pharmacological agent may be utilized in aerosol formulation or an analogous formulation to be administered via inhalation or analogous means. The pharmacological agent employed in the practice of the present invention may be formulated into pressurized acceptable propellants such as dichlorodifluoromethane, propane, nitrogen and the like.

A pharmacological agent of the invention may be delivered transdermally, by a topical route, formulated as applicator sticks, solutions, suspensions, emulsions, gels, creams, ointments, pastes, jellies, paints, powders, and aerosols. For example, embodiments may include a pharmacological agent in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agents are retained. The base or matrix layer may be operatively associated with a support or backing. Pharmacological formulations suitable for transdermal administration may also be delivered by iontophoresis and may take the form of an optionally buffered aqueous solution of the pharmacological compound. Suitable formulations may include citrate or bis/tris buffer (pH 6) or ethanol/water and contain a suitable amount of active ingredient.

A pharmacological agent of the invention may also be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

A pharmaceutical formulation of the invention may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological formulations of the subject invention may be useful for parenteral administration, such as intravenous ("IV") administration, intramuscular ("IM"), subcutaneous ("SC" or "SQ"), mucosal. The formulations for administration may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

In certain embodiments, the pharmacological formulations of the invention may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include a pharmacological agent administered as liposomal formulations of the pharmacological agent. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

Embodiments of the pharmacological agent employed in the practice of the subject invention may include pharmaceutical compositions that may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agent, the pharmaceutical compositions of the subject invention may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological compositions may, though not always, contain microbial preservatives. Microbial preservatives that may be employed include, but are not limited to, methylparaben, propylparaben, and benzyl alcohol. The microbial preservative may be employed when the pharmacological formulation is placed in a vial designed for multidose use. Pharmaceutical compositions for use in practicing the subject methods may be lyophilized using techniques well known in the art.

Pharmaceutically acceptable excipients, such as vehicles, adjuvants, carriers or diluents, that may be employed in the subject invention are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of a pharmacological agent using a pharmacological delivery device such as, but not limited to, pumps (implantable or external devices and combinations of both (e.g., certain components are implantable and others may be external to the body such as controls for the implantable components), epidural injectors, syringes or other injection apparatus, catheter and/or reservoir operatively associated with a catheter, etc. For example, in certain embodiments a delivery device employed to deliver a given pharmacological agent to a subject may be a pump, syringe, catheter or reservoir operably associated with a connecting device such as a catheter, tubing, or the like. Containers suitable for delivery of a pharmacological agent to a pharmacological agent administration device include instruments of containment that may be used to deliver, place, attach, and/or insert the pharmacological agent into the delivery device for administration of the pharmacological agent to a subject and include, but are not limited to, vials, ampules, tubes, capsules, bottles, syringes and bags. Embodiments may also include administration of a pharmacological agent via a biodegradable implant drug delivery device. Such may be accomplished by employing syringes to deposit such a biodegradable delivery device under the skin of a subject. The implants degrade completely, so that removal is not necessary.

Embodiments may include employing an electrode to deliver a pharmacological agent to a subject. For example, an electrode may be used that has a small port at its tip which is connected to a reservoir or pump containing a pharmacological agent. The pharmacological agent delivery electrode may be implanted using any suitable technique such as surgical cut down, laproscopy, endoscopy, percutaneous procedure, and the like. In certain embodiments a reservoir or pump may also be implanted in the subject's body. The pharmacological agent delivery electrode, or other analogous device, may be controllable such that the amount of pharmacological agent delivered, the rate at which the pharmacological agent may be delivered, and the time period over which the pharmacological agent may be delivered, etc., may be controllable and may be adjusted.

In certain embodiments, the pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological formulations include, but are not limited to, formulations that include one or more active pharmacological agents and physiological saline solution (optionally including other typical ingredients such as other active agents and buffers).

As noted above, in pharmaceutical dosage forms, a given pharmacological agent may be administered alone or with or in appropriate association, as well as in combination, with other pharmaceutically active compounds. As used herein, "administered with" means that a given pharmacological agent and at least one other adjuvant (including one or more other different pharmacological agents) are administered at times sufficiently close that the results observed are indistinguishable from those achieved when the pharmacological agent and at least one other adjuvant are administered at the same point in time. The pharmacological agent and at least one other adjuvant may be administered simultaneously (i.e., concurrently) or sequentially. Simultaneous administration may be carried out by mixing a given pharmacological agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant are administered at the same point in time or immediately following one another. In the latter case, the pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) calculated in an amount sufficient to produce the desired effect in association with a pharmaceutically acceptable diluent, carrier or vehicle. The specifications for the unit dosage forms of a given pharmacological agent employed in the practice of the present invention depend on, for example, the particular pharmacological agent employed and the effect to be achieved, the pharmacodynamics associated with the particular pharmacological agent in the subject, etc.

As noted above, those of skill in the art will readily appreciate that dose levels may vary as a function of the specific pharmacological agent, the nature of the delivery vehicle, and the like. Dosages for a given pharmacological agent are readily determinable by those of skill in the art by a variety of means. Exemplary dosage levels are provided herein and are not to be construed to limit the scope of the invention in any manner.

A wide variety of different pharmacological agents may be employed in the practice of the subject methods, where the particular pharmacological agent or combination of pharmacological agents employed will depend on, e.g., the subject being treated, the condition being treated, duration of treatment, whether it is desired to increase activity in the parasympathetic system and/or increase activity in the sympathetic system and/or decrease activity in the sympathetic system and/or decrease activity in the parasympathetic system, etc. Representative pharmacological agents (and analogs and salts thereof) include, but are not limited to, one of more of the following:

beta-blockers (e.g., atenolol (e.g., as sold under the brand names TENORMIN), betaxolol (e.g., as sold under the brand name KERLONE), bisoprolol (e.g., as sold under the brand name ZEBETA), carvedilol (e.g., as sold under the brand name COREG), esmolol (e.g., as sold under the brand name BREVIBLOC), labetalol (e.g., as sold under the brand name NORMODYNE), metoprolol (e.g., as sold under the brand name LOPRESSOR), nadolol (e.g., as sold under the brand name CORGARD), pindolol (e.g., as sold under the brand name VISKEN), propranolol (e.g., as sold under the brand name INDERAL), sotalol (e.g., as sold under the brand name BETAPACE), timolol (e.g., as sold under the brand name BLOCADREN), carvedilol, and the like);

aldosterone antagonists (e.g., spironolactone, eplerenone, and the like);

angiotensin II receptor blockades (e.g., candeartan (e.g., available under the brand name ALTACAND), eprosarten mesylate (e.g., available under the brand name TEVETAN), irbesartan (e.g., available under the brand name AVAPRO), losartan (e.g., available under the brand name COZAAR), etelmisartin (e.g., available under the brand name MICARDIS), valsartan (e.g., available under the brand name DIOVAN), and the like);

angiotensin converting enzyme ("ACE") inhibitors (e.g., benazapril (e.g., available under the brand name LOTENSIN), captopril (e.g., available under the brand name CAPOTEN) enalapril (e.g., available under the brand name VASOTEC) fosinopril (e.g., available under the brand name MONOPRIL) lisinopril (e.g., available under the brand name PRINIVIL) moexipril (e.g., available under the brand name UNIVASC) quinapril (e.g., available under the brand name ACCUPRIL) ramipril (e.g., available under the brand name ALTACE) trandolapril (e.g., available under the brand name MAVIK), and the like);

statins (e.g., atorvastatin (e.g., available under the brand name LIPITOR), cerivastatin (e.g., available under the brand name BAYCOL), fluvastatin (e.g., available under the brand name LLESCOL), lovastatin (e.g., available under the brand name MEVACOR), prevastatin (e.g., available under the brand name PRAVACHOL), simvastatin (e.g., available under the brand name ZOCOR), and the like);

triglycerides lowering agents (e.g., fenofibrate (e.g., available under the brand name TRICOR), genfibrozil (e.g., available under the brand name LOPID), and the like);

niacin;

diabetes agents (e.g., acarbose (e.g., available under the brand name PRECOSE), glimepiride (e.g., available under the brand name AMARYL), glyburide (e.g., available under the brand names MICRONASE, DIABETA), metformin (e.g., available under the brand name GLUCOPHASGE), miglitol (e.g., available under the brand name GLYCET), pioglitazone (e.g., available under the brand name ACTOS), repaglinide (e.g., available under the brand name PRANDIN), rosiglitazone (e.g., available under the brand name AVANDIA), and the like);

immunomodulators (e.g., interferon beta-1B (e.g., available under the brand name BETASERON), interferon alfa-2A (e.g., available under the brand name ROFERON-A) interferon alfa-2B (e.g., available under the brand name INTRON-A), interferon alfa-2B and Ribavirin combo pack (e.g., available under the brand name REBETRON), interferon alfa-N3 (e.g., available under the brand name ALFERON N), interferon beta-1A (e.g., available under the brand name AVONEX), interferon beta-1B, interferon gamma immunoregulatory antibodies that bind to or react with one of the following antigens: CD4, gp39, B7, CD19, CD20, CD22, CD401, CD40, CD40L and CD23, rituximab (e.g., available under the brand name RITUXAN), any chemical or radiopharmaceutical linked or conjugated antibodies that bind to or react with one of the following antigens: CD4, gp39, B7, CD19, CD20, CD22, CD401, CD40, CD40L and CD23), and the like);

nicotine;

sympathomimetics (e.g., trimethaphan, clondine, reserpine, guanethidine, and the like);

antihistamines (e.g., available under the brand name BENADRYL, diphenhydramine, available under the brand name ACTIFED, and the like);

cholinergics (e.g., bethanechol, oxotremorine, methacoline, cevimeline, and the like);

acetylcholinesterase inhibitors (e.g., edrophonium, neostigmine, donepezil, tacrine, echothiophate, diisopropylfluorophosphate, demecarium, pralidoxime, galanthamine, tetraethyl pyrophosphate, parathoin, malathion, isoflurophate, metrifonate, physostigmine (and phenylcarbamate of physostigmine such PHENSERINE and its analogues (AchE-1)), rivastigmine, abenonium acetylchol, carbaryl acetylchol, propoxur acetylchol, aldicarb acetylchol, and the like);

magnesium and magnesium sulfates;

calcium channel blockers (e.g., amlodipine besylate (e.g., available under the brand name NORVASC), diltiazem hydrochloride (e.g., available under the brand names CARDIZEM CD, CARDIZEM SR, DILACOR XR, TIAZAC), felodipine plendil isradipine (e.g., available under the brand names DYNACIRC, DYNACIRC CR), nicardipine (e.g., available under the brand name CARDENE SR), nifedipine (e.g., available under the brand names ADALAT CC, PROCARDIA XL), nisoldipine sulfur (e.g., available under the brand name SULAR), verapamil hydrochloride (e.g., available under the brand names CALAN SR, COVERA HS, ISOPTIN SR, VERELAN) and the like);

muscarinics (e.g., muscarine, pilocarpine, and the like);

sodium channel blockers, (e.g., moricizine, propafenone, encainide, flecainide, tocainide, mexiletine, phenytoin, lidocaine, disopyramide, quinidine, procainamide, and the like);

glucocorticoid receptor blockers (e.g., mifepristone, and the like); peripheral andrenergic inhibitors (e.g., guanadrel (e.g., available under the brand name HYLOREL), guanethidine monosulfate (e.g., available under the brand name ISMELIN), reserpine (e.g., available under the brand names SERPASIL, MECAMYLAMINE, HEXEMETHONIUM), and the like);

blood vessel dilators (e.g., hydralazine hydrocholoride (e.g., available under the brand name APRESOLINE), minoxidil (e.g., e.g., available under the brand name LONITEN), and the like);

central agonists (e.g., alpha methyldopa (e.g., available under the brand name ALDOMET), clonidine hydrochloride (e.g., available under the brand name CATAPRES), guanabenz acetate (e.g., available under the brand name WYTENSIN), guanfacine hydrochloride (e.g., available under the brand name TENEX), and the like;

combined alpha and beta-blockers (e.g., carvedilol (e.g., available under the brand name COREG), labetolol hydrochloride (e.g., available under the brand names NORMODYNE, TRANDATE), and the like);

alpha blockers (e.g., doxazosin mesylate (e.g., available under the brand name CARDURA), prazosin hydrochloride (e.g., available under the brand name MINIPRESS), terazosin hydrochloride (e.g., available under the brand name HYTRIN), and the like);

combination diuretics (e.g., amiloride hydrochloride+hydrochlorothiazide (e.g., available under the brand name MODURETIC), spironolactone+hydrochlorothiazide (e.g., Aldactazide), triamterene+hydrochlorothiazide (e.g., available under the brand names DYAZIDE, MAXZIDE) and the like);

potassium sparing diuretics (e.g., amiloride hydrochloride (e.g., available under the brand name MIDAMAR), spironolactone (e.g., available under the brand name ALDACTONE), triamterene (e.g., available under the brand name DYRENIUM), and the like); nitrates (e.g., L-arginine, (e.g., available under the brand names NITROGLYCERIN DEPONIT, MINITRAN, NITROPAR, NITROCINE, NITRO-DERM, NITRO DISC, NITRO-DUR, NITROGARD, NITROGLYCERIN, NITROGLYCERIN T/R, NITRO-TIME, NITROL OINTMENT, NITROLINGUAL SPRAY, NITRONG, NITRO-BID, NITROPRESS, NITRO-PREX, NITRO S.A., NITROSPAN, NITROSTAT, NITROTRANS SYSTEM, NITRO-TRANSDERMAL, NITROTIME, TRANSDERM-NITRO, TRIDIL. PENTAERYTHRITOL TETRANITRATE PERITRATE, PERITRATE S.A. ERYTHRITYL TETRANITRATE CARDILATE ISOSORBIDE DINITRATE/PHENOBARBITAL ISORDIL W/PB ISOSORBIDE MONONITRATE IMDUR, ISMO, ISOSORBIDE MONONITRATE, MONOKET ISOSORBIDE NITRATE DILATRATE-SR, ISO-BID, ISORDIL, ISORDIL TEMBIDS, ISORDIL DINITRATE, ISORDIL DINITRATE LA, SORBITRATE, SORBITRATE SA), and the like);

cyclic nucleotide monophosphodiesterase ("PDE") inhibitors (e.g., vardenafil (e.g., available under the brand name LEVITRA), sildenafil (e.g., available under the brand name VIAGRA) tadalafil (e.g., available under the brand name CIALIS) and the like);

alcohols;

vasopressin inhibitors (e.g., atosiban, and the like);

oxytocin inhibitors (e.g., terbutaline, ritodrine, and the like);

glucagons like peptide 1;

relaxin hormone;

renin inhibitors (e.g., Aliskiren, and the like);

estrogen and estrogen analogues (e.g., estradiols, and the like) and metabolites;

progesterone inhibitors;

testosterone inhibitors;

gonadotropin-releasing hormone analogues (GnRH-As);

gonadotropin-releasing hormone inhibitors (e.g., Leuprolide Acetate, and the like);

type 4 phosphodiesterase inhibitors (PDE4);

vesicular monoamine transport (VMAT) inhibitors (e.g., tetrabenazine, and the like); dipeptidyl peptidase (DP) IV inhibitors (DP4 inhibitors) (e.g., LAF237, P93/01, P32/98, valine pyrrolidide, and the like);

melatonin; and combinations of any of the above agents.

As noted above, one or more of the above-described a pharmacological agents may be employed in the practice of the subject methods and may be of particular use in modulating at least a portion of a subject's autonomic nervous system to increase the parasympathetic activity/sympathetic activity ratio. However, other pharmacological agents may be employed in the practice of the subject methods. For example, following pharmacological agents may be employed in the practice of the subject methods, where one or more of the following pharmacological agents may be of particular use in modulating at least a portion of a subject's autonomic nervous system to increase the sympathetic activity/parasympathetic activity ratio. Representative pharmacological agents (and analogs and salts thereof) that may be employed in the practice of the subject methods (e.g., to modulating at least a portion of a subject's autonomic nervous system to increase the parasympathetic activity/sympathetic activity ratio) include, but are not limited to, one of more of the following:

beta agonists, e.g., dobutamine, metaproterenol, terbutaline, ritodrine, albuterol;

alpha agonists,.e.g., selective alpha 1-adrenergic blocking agents such as phenylephrine, metaraminol, methoxamine; prednisone and steroids, (e.g., available under the brand names CORATN, DELTASONE, LIQUID PRED, MEDI-CORTEN, ORASONE, PANASOL-S, PREDNICEN-M, PREDNISONE INTENSOL);

indirect agents that include norepinephrine, e.g., ephedrine, ampthetamines, phenylpropanolamines, cyclopentamines, tuaminoheptanes, naphazolines, tetrahydrozolines;

epinephrine;

norepinephrine;

acetylcholine;

sodium;

calcium;

angiotensin I;

angiotensin II;

angiotensin converting enzyme I ("ACE I");

angiotensin converting enzyme II ("ACE II");

aldosterone;

potassium channel blockers and magnesium channel blockers, e.g., valproate (sodium valproate, valproic acid), lithium;

cocaine;

amphetamines;

ephedrine;

terbutaline;

dopamine;

doputamine;

antidiuretic hormone ("ADH") (also known as vasopressin);

oxytocin (including PITOCINE);

THC cannabinoids; and combinations thereof

As noted above, embodiments may include administering an effective amount of a first pharmacological agent and an effective amount of at least a second, different pharmacological agent, e.g., concurrently administered, where the two may differ in one or more of a variety of aspects, e.g., dosage, type, route of administration, etc. For example, embodiments may include administering a first type of pharmacological agent and at least one other type of pharmacological agent to provide an enhanced therapeutic effect. By "enhanced therapeutic effect" is meant that at least the initial relief of the particular condition being treated by the first pharmacological agent employed occurs more quickly with a combination of the first pharmacological agent and at least one other different pharmacological agent, as compared to the same doses of each component given alone, or that doses of one or all component(s) are below what would otherwise be a minimum effective dose (a "sub-MED").

Accordingly, embodiments of the subject invention includes treating a subject for a condition by modulating at least a portion of the subject's autonomic nervous system by administering a first pharmacological agent together with at least one other, different pharmacological agent. The pharmacological agents may be concomitantly administered as described above, i.e., they may be given in close enough temporal proximity to allow their individual therapeutic effects to overlap. For example, embodiments of the subject invention may include the co-timely administration of a first pharmacological agent and at least a second, different pharmacological agent. By "co-timely" with respect to drug administration is meant administration of a second pharmacological agent for the treatment of a condition while a first pharmacological agent is still present in a subject's system at an effective amount. It is to be understood that in some instances this will require sequential administration. Alternatively, multiple routes of administration may be employed, e.g., intravenous or subcutaneous injection of a first pharmacological agent may be combined with oral administration of a second, different pharmacological agent.

Embodiments also include pharmaceutical compositions in unit dosage forms that are useful in treating a subject for a condition by modulating at least a portion of a subject's autonomic nervous system and which contain a first pharmacological agent and at least a second, different type of pharmacological agent. In other words, a single drug administration entity or unit dosage form may include two or more pharmacological agents. For example, a single tablet, capsule, dragee, trocheem suppository, syringe, transdermal patch, and the like, combining two or more pharmacological agents would be a unit dosage form. The therapeutic agents present in a unit dosage form may be present in amounts such that, upon administration of one or more unit doses of the composition, a subject may experience a longer lasting efficacy than with the administration of either agent alone. Such compositions may be included as part of a therapeutic package in which one or more unit doses are placed in a finished pharmaceutical container. Labeling may be included to provide directions for using the composition in the treatment of a condition by modulating at least a portion of a subject's autonomic nervous system. The actual amounts of each agent in such compositions will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol. A person of ordinary skill in the art will be able without undue experimentation, having regard to that skill and this disclosure, to determine an effective amount of a particular pharmacological agent for practice of this invention. For example, embodiments may include dosages conventionally administered for the particular pharmacological agents employed, where such dosages are known in the art.

Accordingly, in practicing the subject methods, an effective amount of a pharmacological agent is administered to a subject to treat a condition affecting the subject. As noted above, the particular dosage, mode of administration, treatment times, etc., will vary according to a variety of factors, but will generally fall within the ranges conventionally administered for the particular pharmacological agent employed. As noted above, the dose of pharmacological agent will be different for different subject, condition(s) treated, etc. The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent. Exemplary treatment protocols are now provided.

Electric Energy Applying Devices

As described above, embodiments of the subject invention may include electrically modulating at least a portion of the autonomic nervous system to increase the parasympathetic activity/sympathetic activity ratio. Electrical energy may be employed to increase and/or decrease activity in at least a portion of the autonomic nervous system. For example, embodiments may include electrically modulating at least a portion of the autonomic nervous system to achieve one or more of the following: (1) increasing activity in at least one parasympathetic nerve fiber to achieve an increase in activity in at least a portion of the parasympathetic system, (2) increasing activity in at least one sympathetic nerve fiber to achieve an increase in activity in at least a portion of the sympathetic system, (3) inhibiting activity in at least one parasympathetic nerve fiber to achieve a decrease in activity in at least a portion of the parasympathetic system, and (4) inhibiting activity in at least one sympathetic nerve fiber to achieve a decrease in activity in at least a portion of the sympathetic system. Certain embodiments of the subject invention may include electrically modulating the autonomic nervous system to both increase activity in at least a portion of the autonomic nervous system, e.g., increase activity in at least one parasympathetic nerve fiber, and inhibit activity in at least a portion of the autonomic nervous system, e.g., inhibit activity in at least one sympathetic nerve fiber, or vice versa, to treat a condition. Accordingly, embodiments of the subject methods include providing electrical energy to at least a portion of a subject's autonomic nervous system, where such electrical energy may be excitatory (to increase activity) or inhibitory (to decrease activity) and in certain embodiments may be both excitatory and inhibitory energies.

As noted above, electrical modulation in accordance with the subject invention may be performed prior to and/or at the same time and/or subsequent to any other medical or clinical treatment regime such as any of those described above, for example, pharmacological modulation of at least a portion of the subject's autonomic nervous system.

According to embodiments of the subject invention, electrical modulation is accomplished by at least administering electrical energy to a subject in a manner sufficient to treat the subject for a condition, where the condition may be caused, precipitated or otherwise exacerbated, influenced or affected by the ratio of the parasympathetic activity/sympathetic activity ratio. In other words, activity in at least a portion of the autonomic nervous system may be at a level that is at least contributing to or otherwise affecting or exacerbating a condition such a disease condition in need of treatment, and as such modulation of the autonomic nervous system may be employed to treat the condition.

Methods and devices suitable for use in electrically modulating a portion of subject's autonomic nervous system, and which may be employed in the practice of the subject invention, are described in detail in copending U.S. application Ser. No. 10/661,368, entitled "Treatment of Conditions Through Electrical Modulation of the Autonomic Nervous System", the disclosure of which is herein incorporated by reference.

In general, modulating at least a portion of the autonomic nervous system using electrical energy may be accomplished with the use of an electric energy applying devices (also referred to as electrical energy supplying or delivering devices), such as, e.g., described in the above-noted copending patent application. Once an electric energy applying device is positioned in a suitable position on or about one or more targeted areas of the autonomic nervous system such as one or more parasympathetic nerve fibers and/or one or more sympathetic nerve fibers, electrical energy is applied to the area(s) (e.g., the targeted nerve fiber(s)) for a period of time sufficient to provide the desired modulation of the autonomic nervous system. This period of time will vary depending on the area (e.g., the nerve fiber) being treated, the condition being treated, the particulars of the device used, etc.

As described in greater detail below, certain embodiments include simultaneously monitoring (i.e., in "real time") the parasympathetic activity and/or sympathetic activity such that electrical energy is applied until the desired increase in parasympathetic activity/sympathetic activity ratio is observed. Still further, in many embodiments once the desired ratio is achieved, electrical energy may be repeatedly applied thereto one or more times to maintain the desired state such that the subject methods may be repeated one or more times, i.e., the subject methods include chronic administration of electrical energy to at least one area of the autonomic nervous system. For example, in certain embodiments electrical energy (e.g., intermittent mild electrical pulses) may be delivered to a given area of the autonomic nervous system twenty-four hours a day for a period of days, weeks, months, years or even the entire lifetime of the subject.

During the period of time that a given area of the autonomic nervous system is electrically modulated, the electrical energy may be applied substantially continuously, including continuously, or intermittently (i.e., pulsed or periodic), where in many embodiments the electrical energy is in the form of electrical pulses. In other words, in certain embodiments a given area of the autonomic nervous system (e.g., a given nerve fiber) may be continuously contacted with electrical energy during the above-described period of time and in certain other embodiments a given area of the autonomic nervous system (e.g., a given nerve fiber) may be pulsed or intermittently contacted with electrical energy during the period of time described above.

In accordance with embodiments of the subject methods to electrically modulate at least one area of the autonomic nervous system, once operatively positioned the electrical energy applying device is activated to provide an electrical signal to the targeted area such as to one or more nerve fiber(s) in a manner to modulate the autonomic nervous system, e.g., to increase the parasympathetic activity/sympathetic activity ratio, at least in the particular area being contacted with electrically energy and in certain instances in adjacent areas or in the entire autonomic system, e.g., systemically in certain instances. For example, many nerve fibers are in close proximity and thus application of electrical energy to one nerve fiber may also increase or decrease activity in one or more other nerve fibers, e.g., nerve fibers in close proximity thereto.

Activation of the electrical energy supplying device directly applies the electrical output of the device, i.e., electrical energy, to the targeted area. For example, electrodes may be positioned to direct electrical impulses to specific nerve fibers, etc. The exact parameters of the protocol may vary depending on the particular subject, condition being treated, etc. An electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Monopolar or multipolar technologies may be employed.

For example, to increase activity in a portion of the autonomic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

To inhibit activity or conduction in a portion of the sympathetic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 50 Hz to about 2500 Hz. In certain embodiments a pure d-c voltages may be employed. The pulse width may range from about 1 microseconds to about 2000 microseconds or more, e.g., from about 10 microseconds to about 2000 microseconds, e.g., from about 15 microseconds to about 1000 microseconds, e.g., from about 25 microseconds to about 1000 microseconds. The electrical energy may be applied for at least about 1 millisecond or more, e.g., about 1 second, e.g., about several seconds, where in certain embodiments the electrical energy may be applied for as long as about 1 minute or more, e.g., about several minutes or more, e.g., about 30 minutes or more may be used in certain embodiments.

The time period for modulating at least a portion of a subject's autonomic nervous system using electrical energy may be analogous to that described above for pharmacologically modulating at least a portion of a subject's autonomic nervous system.

A variety of different devices for applying electrical energy to increase or inhibit at least a portion of the autonomic nervous system in accordance with the subject invention may be employed as described in the above referenced, copending U.S. application Ser. No. 10/661,368, the disclosure of which is herein incorporated by reference. Electrical energy delivering devices that may be used to practice the subject invention may be positioned directly on a targeted area, e.g., positioned below the skin of a subject directly on or adjacent a portion of the autonomic nervous system (e.g., one or more nerve fibers) such as an implantable device, or may be an external device (i.e., some or all of the device may be external to the subject). In accordance with embodiments of the subject invention, one or more electrodes or electrical contacts may be positioned directly on or adjacent a targeted area of the autonomic nervous system, i.e., directly on or adjacent a portion of the parasympathetic and/or sympathetic system, where the one or more electrodes may be surgically implanted directly on or adjacent a targeted nerve fiber of a subject. In further describing embodiments of the subject invention, a single electrode is described however it is to be understood that multiple electrodes may be employed and features and characteristics of the single electrode described herein are applicable to any other electrodes that may be employed in the practice of the subject invention.

Electrical energy delivering devices that may be employed in the practice of the subject methods typically include a stimulator (or inhibitor) such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of a representative electrode suitable for use in the subject methods is applicable to other electrodes that may be employed.

The electrode employed in the subject invention is typically controllable to provide output signals that may be varied in voltage, frequency, pulse width, current and intensity. The electrode is typically one that provides both positive and negative current flow from the electrode and/or is capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output is provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Implantable generators analogous to a cardiac pacemaker may be used in certain embodiments.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed.

A variety of methods may be used to endoscopically or surgically implant the electrode on or adjacent at least a portion of the autonomic nervous system such as on or adjacent one or more nerve fibers of the parasympathetic nervous system and/or sympathetic system, where such methods are known to those of skill in the art. Because some nerve fibers may be in very close proximity to one another within a very small area, an analogous technique may generally be employed to provide operable placement of the electrode on or adjacent to any targeted area of the autonomic nervous system.

A controller or programmer is also typically included in an electrical energy supplying device. The programmer is typically one or more microprocessors under the control of a suitable software program. Other components of the programmer will be apparent to those of skill in the art, e.g., analog to digital converter, etc.

The electric energy supplying device employed in the practice of the subject methods may be pre-programmed for desired parameters. In many embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

An open-loop controlled system may be employed. In an open-loop system, the physician or patient may at any time manually or by the use of pumps or motorized elements adjust treatment parameters such as pulse amplitude, pulse width, pulse frequency, or duty cycle. Optionally, the a closed-loop control system may be employed which may automatically adjust the electrical parameters in response to a sensed symptom or an important related symptom indicative of the extent of the condition being treated. Under a closed-loop feedback system to provide automatic adjustment of parameters of the electrodes, a sensor that senses a condition of the body is utilized. In certain embodiments, such a condition may be one or more aspects of the autonomic nervous system, etc. More detailed descriptions of sensors that may be employed in the practice of the subject invention, and other examples of sensors and feedback control techniques that may be employed are disclosed in U.S. Pat. No. 5,716,377, which is incorporated herein by reference.

Operative placement of a suitable electric energy supplying device may be accomplished using any suitable technique. In general, such placement includes localization of an area of the autonomic nervous system, positioning the electrode on or adjacent the area and attaching the electrode to a power source. However, with regard to attaching the electrode to a power source, it should be understood that electrodes may be employed which make the implantation and/or attachment of a separate power source unnecessary. For example, an electrode may be employed which includes its own power source, e.g., which is capable of obtaining sufficient power for operation from surrounding tissues in the patient's body or which may be powered by bringing a power source external to the patient's body into contact with the patient's skin, or may include an integral power source, and the like. In such instances, the surgical procedure may be completed upon implantation of the electrode on or adjacent to the area of interest.

An electrode introducer needle may be employed to implant the electrode on or proximate to the area of interest.

The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical procedure during the localization of a given area, e.g., to assist in determining a suitable entry point for the insertion of the electrode.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is suitably positioned, the stylet is withdrawn from the electrode introducer needle. A "test" electrode, if employed, used to test the placement of the electrode introducer needle may then be positioned within the central channel of the needle. If a "test" electrode is not employed, the electrode that is to be employed to modulate the autonomic nervous system may then be positioned within the central channel of the needle. The electrode may then be advanced to the distal tip of the needle to place the electrode on or proximate to the area of interest.

In certain embodiments, the "test" electrode, if employed, may be a radiofrequency stimulating electrode suitable to electrically stimulate the tissue at the end of the tip of the electrode and verify its position physiologically within the patient, which may be a different electrode than that ultimately implanted within the patient. A suitable radiofrequency stimulating electrode may be 10 cm with a 2-mm non-insulated active tip. Once the "test" electrode is inserted through the electrode introducer needle with its electrical contacts exposed, it may then be connected to an electrical stimulus/lesion generator for electrical stimulation.

The frequency of stimulation may be set at any suitable frequency, e.g., at about 50 Hz, and the voltage may be gradually increased until the subject reports acknowledgement of application of electrical current, e.g. reports stimulation, of or about the area of interest of the autonomic nervous system. Repositioning of the electrode may be performed as necessary.

If a "test" electrode is employed to test the placement of the electrode introducer needle and as such is different from the electrode to be employed to modulate the autonomic nervous system (i.e., the electrode to be implanted if it is desired to implant the electrode that will be employed to modulate the autonomic nervous system), the "test" electrode may then be removed from the electrode introducer needle while the needle is held firmly in place to prevent displacement. The electrode to be implanted may then be inserted through the central channel of the needle while the needle is held in place at the hub. Once the electrode to be implanted is in position, fluoroscopic imaging and electrical stimulation may be employed to verify the correct positioning of the needle and the electrode. Alternatively, if the electrode used to test the placement of the electrode introducer needle is the electrode to be implanted, the electrode may be left in the final test position.

Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the body. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control or stimulate the electrode may be surgically implanted in the desired region by procedures known in the art, such as have been applied in surgical neuromodulation therapies used to treat Parkinson's disease.

Regardless of how the autonomic nervous system is modulated (pharmacologically, electrically, etc.), certain embodiments of the subject methods may also include detecting, monitoring, observing, etc., information related to one or more aspects of the autonomic nervous system such as a physical and/or chemical aspect, e.g., activity, balance, etc., in at least a portion of the autonomic nervous system, e.g., in at least a portion of the sympathetic nervous system and/or parasympathetic system, and evaluating this information to determine the state of the autonomic nervous system, e.g., the parasympathetic activity and/or sympathetic activity. Once the state of the autonomic nervous system is determined, it may be evaluated in regards to whether the autonomic nervous system is in need of modulation, i.e., whether the parasympathetic activity/sympathetic activity ratio needs to be increased to treat a condition such that this analysis may be employed as a "trigger" to modulating or further modulating at least a portion of the autonomic nervous system wherein modulation may not be otherwise performed unless the analysis determined such is necessary. One or more aspects of the condition being treated may also be detected and/or monitored such as any suitable manifestation of the condition.

Accordingly, collecting and evaluating this type of data and relating it to whether autonomic nervous system modulation is required may be employed as a "trigger" to modulating at least a portion of the autonomic nervous system (e.g., performed prior to, during or following a particular autonomic nervous system modulation protocol whether performed using pharmacological methods, electrical energy methods or other methods) such that such data may indicate whether, when, etc., modulation is required—if at all. For example, in certain embodiments modulation of at least a portion of a subject's autonomic nervous system may not be performed unless one or more aspects of the autonomic nervous system are detected and indicate such modulation is necessary. Any suitable physical and/or chemical aspect or indicator of the autonomic nervous system may be employed, e.g., amounts of T helper cells (Th1 and/or Th2), conduction, catecholamine levels, heart rate variability ("HRV"), action potentials, QT interval, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, particular hormonal levels, e.g., associated with a particular phase of the menstrual cycle, may be detected. In certain embodiments, detection may include detecting the activity or function of a particular organ or system under the control of the autonomic nervous system. Other exemplary measurements may include, but are not limited to, plasma volume, effective renal plasma volume, effective renal blood flow, norepinephrine, and concentrations of rennin-angiotensin-aldosterone system hormones, etc. Any suitable detection means may be employed to detect relevant information about the autonomic nervous system.

In certain embodiments, a control feedback loop is provided. For example, during or following a particular treatment regimen, the sympathetic activity and/or parasympathetic activity may be monitored, observed, detected, etc., e.g., by sensing conduction in at least a portion of the sympathetic system and/or parasympathetic system by any suitable method. Other methods that may be employed to monitor the autonomic system include, but are not limited to, amounts of T helper cells (Th1 and/or Th2), neurography, continuous or serial measurements of circulating catecholamine levels, chronotropic, inotropic, and vasodilator responses, heart rate variability ("HRV"), particular hormonal levels, post-ganglionic action potentials, QT interval, and the like. For example, in certain embodiments HRV measures such as low frequency peak ("LF"), high frequency peak ("HF"), and the LF/HF ratio may be used to monitor the autonomic nervous system, as well as, but not limited to, plasma volume, effective renal plasma volume, effective renal blood flow, norepinephrine, and concentrations of rennin-angiotensin-aldosterone system hormones. For example, a sensor suitable for detecting nerve cell or axon activity that are related to the autonomic nervous system may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products.

Embodiments include utilizing a feedback system in such a manner that, if the desired increase/decrease in sympathetic and/or parasympathetic activity is not achieved, the same or a different treatment protocol for modulating the activity of the autonomic nervous system activity may be performed. For example, in those instances where a different modulation protocol is performed from a first modulation protocol, one or more of the treatment parameters may be modified. For example, if a first modulation protocol included pharmacological modulation, a second, different modulation protocol may be employed, e.g., a different pharmacological agent may be employed instead or in addition to the first, where the differences may include dosage, type, mode of administration, etc., or the second protocol may include an electrical modulation protocol. In those instances where a different protocol is performed from a first, electrical energy modulation protocol, one or more of the treatment parameters may be modified for a second, different electrical modulation protocol, e.g., a different electrical energy protocol may be employed instead of or in addition to the first, where the differences may include voltage, frequency, pulse width, etc., or the second protocol may include a pharmacological modulation protocol.

Certain embodiments may include simultaneously monitoring, detecting, observing, etc., (i.e., in "real time") the sympathetic activity and/or parasympathetic activity such that modulation of at least a portion of the autonomic nervous system may be performed to treat a condition and the result of the modulation may be observed and/or monitored, e.g., at least once, continuously or intermittently or periodically and in certain embodiments until the desired increase or inhibition in activity is observed or longer. Still further, in many embodiments once the desired autonomic nervous system modulation is achieved the same or different modulation treatment protocol may be performed thereafter at least one time and may be for a period of time, e.g., one or more times, to maintain the desired state such that embodiments of the subject methods may be repeated one or more times.

The above-described methods find use in a variety of different applications, where representative applications are described in greater detail below.

Utility

The subject methods find use in a variety of applications in which it is desired to treat a subject for a condition, e.g., a condition at least influenced by an abnormality in the subject's autonomic nervous system. In such methods, at least a portion of a subject's autonomic nervous system is modulated in a manner suitable to treat the subject for the condition, e.g., in a manner to increase the parasympathetic activity/sympathetic activity ratio or decrease the parasympathetic activity/sympathetic activity ratio in certain embodiments. As indicated above, in many embodiments of this type of application, the subject methods are employed to treat a condition in the subject in order to achieve a desired therapeutic outcome.

The subject methods find use in the treatment of a variety of different conditions in which an abnormality in a subject's autonomic nervous system exists. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

A variety of subjects are treatable according to the subject methods. In many embodiments the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different conditions, including, but not limited to:

cardiovascular conditions including cardiovascular disease, e.g., atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, paroxysmal supraventricular tachycardia, and the like;

neurodegenerative conditions including neurodegenerative diseases, e.g., Alzheimer's Disease, Pick's Disease, Parkinson's Disease, dementia, delirium, amyotrophic lateral sclerosis, and the like;

neuroinflammatory conditions including neuroinflammatory diseases, e.g., viral meningitis, viral encephalitis, fungal meningitis, fungal encephalitis, multiple sclerosis, charcot joint, schizophrenia, myasthenia gravis, and the like;

orthopedic inflammatory conditions including orthopedic inflammatory diseases, e.g., osteoarthritis, inflammatory arthritis, regional idiopathic osteoporosis, reflex sympathetic dystrophy, Paget's disease, osteoporosis, antigen-induced arthritis, juvenile chronic arthritis, and the like;

lymphoproliferative conditions including lymphoproliferative diseases, e.g., lymphoma, lymphoproliferative disease, Hodgkin's disease, inflammatory pseudomotor of the liver, and the like;

autoimmune conditions including autoimmmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, and the like;

inflammatory conditions, e.g., acute respiratory distress syndrome ("ARDS"), multiple sclerosis, rheumatoid arthritis, juvenile rheumatoid arthritis, juvenile chronic arthritis, migraines, chronic headaches, and the like;

infectious diseases, e.g., sepsis, viral and fungal infections, diseases of wound healing, wound healing, tuberculosis, infection, AIDS, human immunodeficiency virus, and the like;

pulmonary conditions including pulmonary diseases, e.g., tachypnea, fibrotic lung diseases such as cystic fibrosis and the like, interstitial lung disease, desquamative interstitial pneumonitis, non-specific interstitial pneumonitis, intrapulmonary shunts; lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like;

transplant-related conditions such as transplant related side effects such as transplant rejection, transplant-related tachycardia, transplant related renal failure, transplant related bowel dysmotility, transplant-related hyperreninemia, and the like;

gastrointestinal conditions including gastrointestinal diseases, e.g., hepatitis, xerostomia, bowel mobility, peptic ulcer disease, constipation, ileus, irritable bowel syndrome, post-operative bowel dysmotility, inflammatory bowel disease, typhilitis, cholelethiasis, cholestasis, fecal incontinence, cyclic vomiting syndrome, and the like;

endocrine conditions including endocrine diseases, e.g., hypothyroidism, hyperglycemia, diabetes, obesity, syndrome X, insulin resistance, polycystic ovarian syndrome ("PCOS"), and the like;

genitourinary conditions including genitourinary diseases, e.g., bladder dysfunction, renal failure, erectile dysfunction, hyperreninemia, hepatorenal syndrome, pulmonary renal syndrome, incontinence, arousal disorder, menopausal mood disorder, premenstrual mood disorder, renal tubular acidosis, pulmonary renal syndrome, and the like;

skin conditions including skin diseases, e.g., wrinkles, cutaneous vasculitis, psoriasis, rash; and the like;

aging associated conditions including aging associated diseases, e.g., shy dragers, multi-system atrophy, age related inflammation conditions, cancer, aging, and the like;

neurologic conditions including neurologic diseases such as epilepsy, depression, schizophrenia, seizures, stroke, insomnia, cerebral vascular accident, transient ischemic attacks, stress, bipolar disorder, concussions, post-concussive syndrome, cerebral vascular vasospasm, central sleep apnea, obstructive sleep apnea, sleep disorders, headaches including chronic headaches, migraines, acute disseminated encephalomyelitis ("ADEM"), and the like;

pediatric conditions, including pediatric diseases, e.g., respiratory distress syndrome, sudden infant death syndrome, hirschsprung disease, bronchopulmonary dysplasia, congenital megacolon, ananglionosis, juvenile rheumatoid arthritis, juvenile chronic arthritis, and the like;

Th-2 dominant conditions including Th-2 dominant diseases, e.g., typhilitis, osteoporosis, lymphoma, myasthenia gravis, lupus, and the like;

conditions, including diseases, that cause hypoxia, hypercarbia, hypercapnia, acidosis, acidemia, Chronic Obstructive Pulmonary Disease ("COPD"), emphysema, any chronic lung disease that causes acidosis, acute pulmonary embolism, sudden adult death syndrome ("SADS"), chronic pulmonary embolism, pleural effusion, cardiogenic pulmonary edema, non-cardiogenic pulmonary edema, acute respiratory distress syndrome (ARDS), neurogenic edema, hypercapnia, acidemia, asthma, renal tubular, asthma, acidosis, chronic lung diseases that cause hypoxia, hypercarbia or hypercapnia, and the like;

OB-GYN conditions including OB-GYN diseases, e.g., amniotic fluid embolism, menopausal mood disorders, premenstrual mood disorders, pregnancy-related arrhythmias, fetal stress syndrome, fetal hypoxia, amniotic fluid embolism, gestational diabetes, pre-term labor, cervical incompetence, fetal distress, peri-partum maternal mortality, peripartum cardiomyopathy, labor complications, premenstrual syndrome, dysmenorrheal, endometriosis, and the like;

sudden death syndromes, e.g., sudden adult death syndrome, sudden infant death syndrome, and the like;

menstrual related disorders, e.g., pelvic pain, dysmenorrheal, gastrointestinal disease, nausea, and the like;

peripartum and pregnancy related conditions, e.g., peripartum cardiomyopathy, and the like;

fibrosis;

post-operative recovery conditions such as post-operative pain, post operative ileus, post-operative fever, post-operative nausea, and the like;

post-procedural recovery conditions such as post-procedural pain, post procedural ileus, post-procedural fever, post-procedural nausea, and the like;

chronic pain;

trauma;

hospitalization;

glaucoma;

male infertility;
disorders of thermoregulation;
respiratory sinus arrhythmia;
VQ mismatch;
fibromyalgia; and the like.

Other conditions may also be treated in accordance with the subject invention. Embodiments of the subject invention include treating one or more conditions, sequentially or at the same time, in accordance with the subject invention.

As noted above, a variety of conditions may be treated according to the subject invention. In certain embodiments, a subject may be treated for a condition by modulating at least a portion of the subject's autonomic nervous system to increase the parasympathetic activity/sympathetic activity ratio.

In certain embodiments, a subject may be treated for a condition by modulating at least a portion of the subject's autonomic nervous system to increase the sympathetic activity/parasympathetic activity ratio. For example, conditions that may be treated according to the subject invention by increasing the sympathetic activity/parasympathetic activity ratio include, but are not limited to: infertility, early pregnancy loss, spontaneous abortion, subfertility, failure of implantation, amenorrhea, luteal insufficiency, dysmenorrheal, pelvic pain, depression, bipolar disorder, bacterial vaginosis, obesity, and multiple sclerosis.

Conditions that promote maladaptive sympathetic bias may be treated in accordance with the subject invention. The inventors of the subject invention have unexpectedly realized that maladaptive sympathetic bias is a distinct syndrome that may be implicated in a number of fatal or potentially fatal conditions. As described above, normally the sympathetic drive is an adaptive response to dynamic physiological demands of the body. Under certain conditions, the response may become maladaptive. The inventors of the subject invention have realized that dramatic impacts on the health and well-being of an individual, in certain instances, may be related to acute sympathetic challenge in the context of background chronic sympathetic bias.

Chronic sympathetic bias may occur in various situations. For example, it may occur when the normal sympathetic bias fails to correct a precipitating respiratory or metabolic abnormality. The inventors of the subject invention have realized that conditions such as sudden infant death syndrome ("SIDS"), sudden adult death syndrome ("SADS") including sudden death among pregnant women, obstructive sleep apnea ("OSA") and congestive heart failure ("CHF") may fall in this category and thus are conditions that may be treated, or prevented, by the subject invention. Furthermore, sustained sympathetic bias is also noted during pregnancy, presumably as an adaptive response. Some diseases, such as pheochromocytoma, are intrinsically adrenergic. Sympathetic bias may also be a maladaptive component of the aging process attributable to an inexorable functional decline in autonomic regulatory systems. In the context of sympathetic bias, the inventors have realized that an acute sympathetic episode, as a centrally or peripherally mediated response to acute behavioral, metabolic, or physiologic stressors such as fear, injury, hypoxia, hypercarpnia, acidosis, sleep arousal, and physical activity, may increase the likelihood of fatal arrhythmias, QT-related and otherwise.

For example, conditions related to chronic or acute hypoxia, hypercarpnia and acidosis, including obstructive sleep apnea ("OSA") and other chronic conditions that disturb pO2, pCO2 and pH such as chronic obstructive pulmonary disease ("COPD"), primary pulmonary hypertension ("PPHTN"), secondary pulmonary hypertension ("SPHTN") and the like, may be treated in accordance with the subject invention. Specifically, the inventors of the subject invention have discovered that excess sympathetic activity relative to parasympathetic activity elicited through, or rather a centrally or peripherally mediated response to, various changes in pO2, pH and pCO2, accounts for many of the physiological consequences of OSA and other chronic conditions that disturb pO2, pCO2 and pH. For example, the inventors have realized that excess sympathetic activity both directly and indirectly (through stimulating inflammation) accounts for the systemic hypertensive disease observed in individual's suffering from OSA. The inventors have realized that many of the inflammatory consequences of OSA, such as hypertension, atherosclerotic disease and insulin resistance are also mediated through excess sympathetic activity relative to parasympathetic activity. Accordingly, the subject methods may be employed to treat OSA and the associated inflammatory conditions, as well as other chronic conditions that disturb pO2, pCO2 and pH levels such as COPD, PPHTN, SPHTN, and the like, by increasing parasympathetic activity relative to sympathetic activity.

As noted above, the subject methods may be employed to treat or rather prevent sudden infant death syndrome ("SIDS") and sudden adult death syndrome ("SADS"), including sudden death amongst pregnant women. In this regard, the inventors of the subject invention have discovered that in certain instances sympathetic bias may be implicated in SIDS and SADS.

More specifically, the inventors of the subject invention have unexpectedly realized that a maladaptive shift to sympathetic bias may be a key determinant of SIDS. Heart rate variability (HRV) is often used as a measure of autonomic balance. Decreased HRV, indicating sympathetic bias, has been observed in patients with central hypoventilation and in infants who have later succumbed to SIDS (see for example Edner A, Katz-Salamon M, Lagercrantz H, Ericson M, Milerad J. Heart rate variability in infants with apparent life-threatening events. Acta Paediatr. 2000 November;89(11): 1326-9). This finding is consistent with other conditions of hypoxia such as respiratory distress syndrome and prenatal hypoxia which decrease HRV and induce tachycardia (see for example Aarimaa T, Oja R. Transcutaneous PO2, PCO2 and heart rate patterns during normal postnatal adaptation and respiratory distress. Early Hum Dev. 1988 January;16(1):3-11), both indicators of sympathetic bias. Infants who experience near-miss SIDS demonstrate tachycardia and decreased HRV (see for example Reid G M. Sudden infant death syndrome: neonatal hypodynamia (reduced exercise level). Med Hypotheses. 2001 March;56(3):280-5). Food regurgitation and diaphoresis associated with SIDS may reflect excess sympathetic activity (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. 2001 April;107(4):693-8; Uchino M, Ishii K, Kuwahara M, Ebukuro S, Tsubone H. Role of the autonomic nervous system in emetic and cardiovascular responses in Suncus murinus. Auton Neurosci. 2002 Sep. 30;100(1-2):32-40).

Inciting causes of sympathetic bias may be manifold. Hyperthermia and fever, both of which have known associations with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. April 2001; 107(4):693-8) are hyperadregnergic states (see for example Rowell L B. Hyperthermia: a hyperadrenergic state. Hypertension. 1990 May;15(5):505-7). Infection and inflammation, which are associated with SIDS (see for example Krous H F, Nadeau J M, Silva P D, Blackbourne B D. A comparison of respiratory symptoms and inflammation in sudden infant death syndrome and in accidental or inflicted infant death. Am J Forensic Med Pathol. March 2003; 24(1): 1-8.), are also potential causes of sympathetic bias. In certain situations, the adaptive chemoreceptor-mediated sympathetic response of arousal and increased respiration may fail to correct the underlying hypoxia, hypercapnia, and acidosis, leading to a maladaptive sympathetic bias. The association of prone sleeping position, obstructive sleep apnea, and other respiratory conditions with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; American Academy of Pediatrics, Task Force on Infant Sleep Position and Sudden Infant Death Syndrome. Changing concepts of sudden infant death syndrome: implications for infant sleeping environment and sleep position. Pediatrics. 2000; 105 :650-656; Hoffman H J, Damus K, Hillman L, Krongrad E. Risk factors for SIDS: results of the National Institute of Child Health and Human Development SIDS Cooperative Epidemiological Study. Ann NY Acad Sci 1988; 533: 13-30) may exemplify this phenomenon. In infants with OSA, as with their adult counterparts, the sympathetic bias can exacerbate sleep disturbance and can trigger insomnia (see for example Harrison G A. Stress, catecholamines, and sleep. Aviat Space Environ Med 1985; 56:651-653; Montagna P, Gambetti P, Cortelli P, Lugaresi E. Familial and sporadic fatal insomnia. Lancet Neuro 2003 March;2(3):167-176.), leading to a pernicious cycle.

Sympathetic bias has an association with QT interval prolongation, a risk factor for sudden cardiac death in adults (see for example Esposito K, Marfella R, Gualdiero P, Carusone C, Pontillo A, Giugliano G, Nicoletti G, Giugliano D. Sympathovagal Balance, Nighttime Blood Pressure, and QT Intervals in Normotensive Obese Women. Obes Res. 2003 May; 11(5):653-9). Sympathetic bias may predispose infants to similar risks. A significant association between prolonged QT interval and SIDS victims or those who experienced apparent life-threatening event (ALTE) has been noted (see for example Goldhammer E I, Zaid G, Tal V, Jaffe M, Abinader E G. QT dispersion in infants with apparent life-threatening events syndrome. Pediatr Cardiol. 2002 November-December;23(6):605-7; Schwartz P J, Stramba-Badiale M, Segantini A, et al. Prolongation of the QT interval and the sudden infant death syndrome. N Engl J Med. 1998; 338 :1709-1714). Various theories for this association have been proposed, including development-related abnormalities in cardiac sympathetic innervation and genetic predisposition (see for example Stramba-Badiale M, Lazzarotti M, Schwartz P J. Development of cardiac innervation, ventricular fibrillation, and sudden infant death syndrome. Am J Physiol 1992;263: H1514-H1522; Ackerman, M. J., Siu, B. L., Sturner, W. Q., Tester, D. J., Valdivia, C. R., Makielski, J. C., Towbin, J. A. (2001). Postmortem Molecular Analysis of SCN5A Defects in Sudden Infant Death Syndrome. JAMA 286: 2264-2269; Schwartz P J. Cardiac sympathetic innervation and the sudden infant death syndrome: a possible pathogenetic link. Am J Med 1976;60:167-172). The inventors of the subject methods have realized that maladaptive sympathetic response is the key determinant of SIDS, a broader view than that which had been held prior to the inventor's view.

The inventors of the subject invention have also unexpectedly realized that sudden death precipitated by maladaptive sympathetic bias, similar to those seen in infants, may account for a proportion of SADS cases.

While multifactorial in mechanism, conditions such as constipation, insomnia, erectile dysfunction, hypertension are endemic among the aged and are consistent with a broad physiologic bias towards sympathetic function. HRV and baroreflex sensitivity decreases with aging (see for example Stratton J R, Levy W C, Caldwell J H, Jacobson A, May J, Matsuoka D, Madden K. Effects of aging on cardiovascular responses to parasympathetic withdrawal. J Am Coll Cardiol. 2003 Jun.4;41(11):2077-83), consistent with a shift to sympathetic bias. The inventors have realized that, as in SIDS, some cases of SADS may reflect maladaptive chemoreceptor response to hypoxia, hypercapnia, and acidosis, all of which are common conditions seen in the elderly due to myriad of diseases. Examples of chronic diseases that exemplify this phenomenon include renal failure, congestive heart failure, chronic obstructive lung disease ("COPD") and chronic pain (see for example Wiggers H, Botker H E, Egeblad H, Christiansen E H, Nielsen T T, Molgaard H. Coronary artery bypass surgery in heart failure patients with chronic reversible and irreversible myocardial dysfunction: effect on heart rate variability. Cardiology. 2002;98(4):181-5). Heightened sympathetic function is seen in many other conditions including pheochromocytoma, autoimmune conditions, and collagen vascular diseases (see for example Lagana B, Gentile R, Vella C, Giovani A, Tubani L, Mastrocola C, Baratta L, Bonomo L. Heart and autonomic nervous system in connective tissue disorders. Recenti Prog Med. 1997 December;88 (12)579-84; P. K. Stein, P. Nelson, J. N. Rottman et al., Heart rate variability reflects severity of COPD in PiZ alpha-1-antitrypsin deficiency. Chest 113 (1998), pp. 327-333). More broadly, the inventors have realized that attrition of parasympathetic function with aging may be an important but until now, unrecognized, culprit in generalized sympathetic bias of aging. For example, it has been observed that QT interval lengthens with aging and other chronic conditions that promote sympathetic bias such as COPD (see for example Wei, J. Y., Spurgeon, H. A. and Lakatta, E. G. (1984) Excitation-contraction in rat myocardium: alteration with adult aging. Am. J. Physiol. 246, H784-H791; Tukek T, Yildiz P, Atilgan D, Tuzcu V, Eren M, Erk O, Demirel S, Akkaya V, Dilmener M, Korkut F. Effect of diurnal variability of heart rate on development of arrhythmia in patients with chronic obstructive pulmonary disease. Int J Cardiol. 2003 April;88(2-3): 199-206), putting the patient at increased risk of fatal arrhythmias.

Still further, pregnant women may exhibit various signs of sympathetic bias such as hyperemesis, hypertension, and increased cardiac output, and as such may be treated in accordance with the subject invention. More specifically, the inventors of the subject invention have realized that sympathetic bias in pregnant women may be responsible for sudden death in pregnant women. The shift to sympathetic bias may represent adaptations to the physiologic and immunologic demands of gestation (see for example Minagawa M, Narita J, Tada T, Maruyama S, Shimizu T, Bannai M, Oya H, Hatakeyama K, Abo T. Mechanisms underlying immunologic states during pregnancy: possible association of the sympathetic nervous system. Cell Immunol. 1999 Aug. 25; 196(1): 1-13). Pregnancy is associated with QT prolongation, increased plasma catecholamine levels, and decreased HRV, similar to the other augmented sympathetic states that increase risk for sudden death (see for example Gowda R M, Khan I A, Mehta N J, Vasavada B C, Sacchi T J. Cardiac arrhythmias in pregnancy: clinical and therapeutic considerations. Int J Cardiol. April 2003; 88(2-3):129-33; N. D. Averyl, L. A. Wolfe, C. E. Amara, G. A. L. Davies, and M. J. McGrath. Effects of human pregnancy on cardiac autonomic function above and below the ventilatory threshold J Appl Physiol 90: 321-328, 2001; Vol. 90, Issue 1, 321-328, January 2001). While an increase rate of sudden deaths from arrhythmias has been noted in pregnant women and has been attributed to hormonal influences (see for example Wolbrette D. Treatment of arrhythmias during pregnancy. Curr Womens Health Rep. April 2003; 3(2):135-9; Wolbrette D, Naccarelli G, Curtis A, Lehmann M, Kadish A. Gender differences in arrhythmias. Clin Cardiol. 2002 February;25(2):49-56), the subject inventors have realized that sympathetic excess of pregnancy may be a potential cause. The most common manifestation of exaggeration of the normal sympathetic shift in pregnant women may be pre-eclampsia, which accounts for 80% of maternal mortality in developing countries (see for example Conz P A, Catalano C. Pathogenesis of pre-eclampsia. G Ital Nefrol. 2003 January-February;20(1):15-22). Measurement of post-ganglionic action potentials reveal mean sympathetic activity to be three times higher in pre-eclamptic women compared with healthy pregnant women, and two times higher compared with the hypertensive non-pregnant women (see for example Schobel H P, Fischer T, Heuszer K, Geiger H, Schmieder R E. Preeclampsia—a state of sympathetic overactivity. N Engl J Med 1996; 335:1480-1485). HRV is reduced in preeclamptic women (see for example Yang C C, Chao T C, Kuo T B, Yin C S, Chen H I. Preeclamptic pregnancy is associated with increased sympathetic and decreased parasympathetic control of HR. Am J Physiol Heart Circ Physiol. 2000 April;278(4):H1269-73). Autonomic imbalance appears to particularly affect the central nervous system. Seizures, a common morbidity of pre-eclampsia, and acute cerebral vasoconstriction, the most common cause of mortality, may both be viewed as acute adrenergic phenomenon (see for example Novak V V, Reeves L A, Novak P, Low A P, Sharbrough W F. Time-frequency mapping of R-R interval during complex partial seizures of temporal lobe origin. J Auton Nerv Syst. 1999 Sep. 24;77(2-3): 195-202). Seizure is also a common presentation among the aged, with 25% of new cases of epilepsy diagnosed in the elderly (see for example Stephen L J, Brodie M J. Epilepsy in elderly people. Lancet. 2000 Apr. 22; 355(9213):1441-6).

Furthermore, as noted above, the subject invention may be employed to treat or prevent congestive heart failure ("CHF"), another situation in which chronic sympathetic bias may be implicated as an underlying cause.

The inventors of the subject invention have also discovered that, unexpectedly, many conditions of aging are manifestations of sympathetic bias that is unmasked by withdrawal of autonomic function, particularly the parasympathetic system. For example, in regards to employing the subject methods in the treatment of aging associated conditions, the inventors of the subject invention have realized that many clinical consequences of aging are pleotropic manifestations of the loss of parasympathetic function that occurs during post-reproductive senescence. The inventors realized that the loss of parasympathetic function unmasks the baseline sympathetic bias inherent in the end-organs, resulting in the familiar signs of aging including tachycardia, constipation, insomnia, erectile dysfunction, fluid retention, and systemic inflammation. These consequences in turn may contribute to many of the common diseases associated with aging including type-2 diabetes, Alzheimer's, atherosclerosis, and cancer. Maintenance and restoration of parasympathetic function may enable upstream control over the deleterious aspects of inherent end-organ adrenergic bias.

The inventors of the present invention have also realized that loss of parasympathetic tone may also explain the somewhat paradoxical emergence of bradycardia during aging. The cardiac conduction system displays decreased intrinsic function with age, often termed the "sick sinus syndrome". As aging and senescence occurs, the heart loses parasympathetic innervation without concomitant decrease in sympathetic function (see for example Brodde O. E., Konschak U., Becker K. et al. Cardiac muscarinic receptors decrease with age. In vitro and in vivo studies. J Clin Invest 1998 Jan. 15; 101(2): 471-8; Ebert T. J., Morgan B. J., Barney J. A., et al. Effects of aging on baroreflex regulation of sympathetic activity in humans. Am J Physiol 1992 September;263(3 Pt 2):H798-803). The adrenergic excess eventually induces focal inflammation and fibrosis of the conduction system irrespective of ischemic changes (see for example Fujino M., Okada R., Arakwa K. The relationship of aging to histological changes in the conduction system of the normal human heart. Jpn Heart J 1983 January;24(1):13-20). Thus, despite the local sympathetic bias, bradycardia ensues.

The inventors of the subject invention have realized the dysregulation of inflammation resulting from the waning parasympathetic tone may be implicated in the susceptibility of the elderly to many other conditions such as atherosclerotic disease, cancer, osteoporosis, viral infections, allergic conditions, and sepsis. As such, the subject methods may be employed to electrically modulating a subject's autonomic nervous to treat aging-related conditions, including disease conditions.

Devices and Systems

The subject invention also includes devices and systems that may be employed in the practice of the subject methods. The subject systems at least include an electric energy applying device such that they include at least include one electrode for electrically modifying at least a portion of a subject's autonomic nervous system in accordance with embodiments of the subject invention, as described above. In many embodiments, the electric energy applying device is an implantable device, or at least certain components such as one or more electrodes, are implantable. Certain embodiments may include a plurality of electrodes, where some or all may be the same or some or all may be different. For example, at least a first electrode may be provide for electrically stimulating at least a portion of the parasympathetic system and at least a second electrode may be provided for inhibiting activity in at least a portion of the sympathetic system. In certain embodiments, a "test" electrode, as described above, may be included in a system. As noted above, such "test" electrodes may be a radiofrequency stimulating electrode. Still further, one or more electrodes may be included in a system which, instead of or in addition to delivering electric impulses to at least a portion of the autonomic nervous system, delivers an autonomic nervous system pharmacological agent to at least a portion of the autonomic nervous system. Embodiments of systems according to the subject invention may includes an energy source such as a battery or generator, where in certain embodiments the energy source may be implantable, and may also include one or more leads or wires for coupling the one or more electrodes to an energy source.

In certain embodiments, the subject systems may include one or more pharmacological agents for use in modulating at least a portion of the autonomic nervous system. In such embodiments, suitable delivery means may be included in the subject systems, dictated by the particular pharmacological agent as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc. Systems may also include one or more devices for delivering, e.g., implanting, an electric energy applying device or portions thereof to a target site of a subject such as into the body cavity of a subject. For example, an endoscope, introducer needle, and the like, may be provided. Systems may also include one or more imaging or scanning apparatuses such as a fluoroscope, CT scan, and the like.

As described above, a system for use in practicing the subject methods may also include a suitable detector (not shown) for detecting one or more physical and/or chemical aspects related to the autonomic nervous system. The detector at least includes data gathering means. Also provided may be data analysis means where such may be a separate component from or integral with data gathering means, but in many embodiments is operatively coupled to data gathering means, e.g., integral with. In use, data related to one or more aspects of the autonomic nervous system may be collected by data gathering means and forwarded to data analysis means which executes steps necessary to process and evaluate the collected data and determine whether the autonomic nervous system is in need of electrical modulation. Such evaluation may include comparing data to reference values, etc. When present, a detector (or data evaluation means if separate) may be operatively coupled to one or more other elements of a given electrostimulatory device such that results of the determinations of autonomic modulation may automatically trigger (or cease) activation of electrical energy to the autonomic nervous system. For example, the detector may detect heart rate variability and determine that activity in the parasympathetic system and/ore sympathetic system needs to be increased and/or decreased. Accordingly, the electric energy applying device may then be activated to provide the appropriate electrical energy or a drug delivery device may be activated to administer an amount of a drug. Suitable detectors include any detector capable of gathering information about the autonomic nervous system and include both invasive, minimally invasive and non-invasive detectors where in certain embodiments a detector may be an implantable detector. Suitable detectors include, but are not limited to, those capable of collecting data regarding nerve conduction, circulating catecholamine levels, heart rate variability ("HRV"), post-ganglionic action potentials, QT interval, and the like and include, but are not limited to, MRI apparatuses, CT apparatus, neurography apparatuses, cardiovascular monitors, sensors including electrodes, etc.

A computer readable medium having programming stored thereon for practicing the subject methods may also be included in a subject system.

A subject system may also include instructions of use for practicing the subject methods. The instructions may be recorded on a suitable recording medium or substrate. For example, the instructions may be printed on a substrate, such as paper or plastic, etc. As such, the instructions may be present as a package insert, etc. In other embodiments, the instructions are present as an electronic storage data file present on a suitable computer readable storage medium, e.g. CD-ROM, diskette, etc. In yet other embodiments, the systems may include means for obtaining the instructions from a remote source, e.g. via the Internet, are provided. An example of this embodiment is a system that includes a web address where the instructions can be viewed and/or from which the instructions can be downloaded. As with the instructions, this means for obtaining the instructions is recorded on a suitable substrate.

Computer Readable Mediums and Programming Stored Thereon

Any part of the subject methods, e.g., detection, analysis and activation/termination of electrical energy including selecting suitable electrical parameters, may be performed manually or automatically and/or for delivering at least one pharmaceutical agent to a subject For example, the subject invention may include suitable computing means such as suitable hardware/software for performing one or more aspects of the subject methods. For example, one or more aspects of the subject invention may be in the form of computer readable media having programming stored thereon for implementing the subject methods. Accordingly, programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out some or all of the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means (i.e., information collected by data gathering means about the autonomic nervous system) and process that information to determine the state of the autonomic nervous system, e.g., the activity level of the parasympathetic system and/or the sympathetic system and even whether the autonomic nervous system requires modulation, e.g., if the parasympathetic activity is normal or abnormal and/or if sympathetic activity is normal or abnormal, and, if so, the specifics of the modulation that is required. The result of that processing may be communicated to a user, e.g., via audio and/or visual means, e.g., the algorithm may also include steps or functions for generating a variety of autonomic nervous system profile graphs, plots, etc.

The algorithm may be configured to, or otherwise be capable of, directing a microprocessor to activate, i.e., turn "on" and "off" an electric energy applying device for applying energy to at least a part of the autonomic nervous system and/or turn "on" and "off" a device for administering a pharmacological agent, e.g., in response to the above-described determination of the state of the autonomic nervous system. For example, if it is determined that parasympathetic activity needs to be increased or decreased and/or sympathetic activity needs to be increased or decreased, the processor may direct the electric energy applying device to provide the appropriate energy to result in the desired action or may direct a pharmacological administering device to administer a suitable amount of pharmacological agent. Accordingly, a processor may select the appropriate parameters (e.g., frequency, amplitude, etc.) depending on what is required and direct an electric energy applying device or drug delivery device to implement the parameters.

The subject invention may also include a data set of known or reference information stored on a computer readable medium to which autonomic nervous system data collected may be compared for use in determining the state of the autonomic nervous system. The data may be stored or configured in a variety of arrangements known to those of skill in the art.

Kits

Also provided are kits for practicing the subject methods. The subject kits may vary greatly in regards to the components included. The kits may include an electric energy applying device, or device for delivering a pharmacological agent to a subject. In certain embodiments, an implantable electric energy applying device, or at least certain components such as one or more electrodes, of an electric energy applying device may be provided.

Kits according to the subject invention may also include an energy source such as a battery or generator, where in certain embodiments the energy source may be implantable, and may also include one or more leads or wires for coupling the one or more electrodes to an energy source.

Devices for delivering, e.g., implanting, an electric energy applying device to a target site of a subject such as into the body cavity of a subject may also be included in the subject kits. For example, an endoscope, introducer needle, and the like may be provided.

The subject kits may also include one or more pharmacological agents for use in practicing the subject methods. The dosage amount of the one or more pharmacological agents provided in a kit may be sufficient for a single application or for multiple applications. Accordingly, in certain embodiments of the subject kits a single dosage amount of a pharmacological agent is present.

In certain other embodiments, multiple dosage amounts of a pharmacological agent may be present in a kit present as discrete unit dosage forms. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit, as noted above. The particular delivery means provided in a kit is dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The subject kits may also include instructions for how to practice the subject methods. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion that the above described invention provides methods, system and kits for modulating at least a portion of the autonomic nervous system to treat a subject for a condition, e.g., a condition caused by an abnormality in the subject's autonomic nervous system, which are easy to use, effective, and may be employed to treat variety of different conditions, including disease conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for a condition comprising electrically modulating at least a portion of said subject's autonomic nervous system to increase the parasympathetic activity/sympathetic activity ratio in a manner effective to treat said subject for said condition, wherein said condition is a neurodegenerative condition chosen from the group of Alzheimer's Disease, Pick's Disease, Parkinson's Disease, dementia, delirium, and amyotrophic lateral sclerosis.

2. A method of treating a subject for a condition comprising electrically modulating at least a portion of said subject's autonomic nervous system to increase the parasympathetic activity/sympathetic activity ratio in a manner effective to treat said subject for said condition, wherein said condition is a lymphoproliferative condition chosen from the group of: lymphoma, lymphoproliferative disease, Hodgkin's disease, and inflammatory pseudotumor of the liver.

3. A method of treating a subject for a condition comprising electrically modulating at least a portion of said subject's autonomic nervous system to increase the parasympathetic activity/sympathetic activity ratio in a manner effective to treat said subject for said condition, wherein said condition is a gastrointestinal condition chosen from the group of: hepatitis, xerostomia, bowel mobility, peptic ulcer disease, constipation, ileus, irritable bowel syndrome, post-operative bowel dysmotility, inflammatory bowel disease, typhilitis, cholelithiasis, cholestasis, fecal incontinence, and cyclic vomiting syndrome.

4. A method of treating a subject for a condition comprising electrically modulating at least a portion of said subject's autonomic nervous system to increase the parasympathetic activity/sympathetic activity ratio in a manner effective to treat said subject for said condition, wherein said condition is a skin condition chosen from the group of: wrinkles, cutaneous vasculitis, rash; and psoriasis.

5. A method of treating a subject for a condition comprising electrically modulating at least a portion of said subject's autonomic nervous system to increase the parasympathetic activity/sympathetic activity ratio in a manner effective to treat said subject for said condition, wherein said condition is a Th-2 dominant condition chosen from the group of: typhilitis, osteoporosis, lymphoma, myasthenia gravis, and lupus.

* * * * *